(12) United States Patent
Reinhardt et al.

(10) Patent No.: US 8,337,843 B2
(45) Date of Patent: *Dec. 25, 2012

(54) TREATMENT OF METASTATIC BREAST CANCER

(75) Inventors: Carsten Reinhardt, Munich (DE); Robert Saller, Munich (DE)

(73) Assignee: Amgen Research (Munich) GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/180,093

(22) Filed: Jul. 11, 2011

(65) Prior Publication Data

US 2012/0009204 A1 Jan. 12, 2012

Related U.S. Application Data

(63) Continuation of application No. 12/162,102, filed as application No. PCT/EP2007/001127 on Feb. 9, 2007, now Pat. No. 7,976,842.

(60) Provisional application No. 60/772,421, filed on Feb. 9, 2006.

(30) Foreign Application Priority Data

Feb. 9, 2006 (EP) .................................... 06002680

(51) Int. Cl.
*A61K 39/395* (2006.01)
(52) U.S. Cl. ................... 424/133.1; 424/174.1
(58) Field of Classification Search .................. None
See application file for complete search history.

(56) References Cited

U.S. PATENT DOCUMENTS

| 2005/0009097 A1 | 1/2005 | Better et al. | 435/7.1 |
|---|---|---|---|
| 2005/0180979 A1 | 8/2005 | Peters et al. | 424/155.1 |
| 2010/0150918 A1 | 6/2010 | Kufer et al. | 424/133.1 |

FOREIGN PATENT DOCUMENTS

WO    WO 2005/080428    9/2005

OTHER PUBLICATIONS

Braun et al., "Monoclonal antibody therapy with Edrecolomab in breast cancer patients: monitoring of elimination of disseminated cytokeratin-positive tumor cells in bone marrow," *Clinical Cancer Research*, 5:3999-4004, 1999.
Casset et al., "A peptide mimetic of an anti-cd4 monoclonal antibody by rational design," *BBRC*, 307: 198-205, 2003.
Edwards et al., "Monoclonal antibody identification and characterization of a Mr 43,000 membrane glycoprotein associated with human breast cancer," *Cancer Res.*, 46 (3): 1306-1317, 1986.
Gastl et al., "Ep-CAM overexpression in breast cancer as a predictor of survival," *Lancet*, 356 (9246): 1981-1982, 2000.
Naundorf et al., "In vitro and in vivo activity of MT201, a fully human monoclonal antibody for pancarcinoma treatment," *Int. J. of Cancer*, 100 (1): 101-110, 2002.
Office Communication issued in U.S. Appl. No. 12/162,102, dated Nov. 1, 2010.
Office Communication issued in European Patent Application No. 07 703 377.7, dated Jun. 28, 2010.
Office Communication issued in Russian Patent Application No. 2008130963/15(038524), dated Nov. 26, 2010. (English translation).
Pascalis et al., "Grafting of "abbreviated" complementarity-determining regions containing spec ificity-determining residues essential for ligand contact to engineer a less immunogenic humanized monoclonal antibody," *The Journal of Immunology*, 169:3076-3084, 2002.
Paul, William E., Editor, *Fundamental Immunology*, 3rd Edition, Raven Press: New York, pp. 292-295, 1993.
PCT International Search Report and Written Opinion, issued in International. Application No. PCT/EP2007/001127, dated Jun. 26, 2007.
Prang et al., "Cellular and complement-dependent cytotoxicity of Ep-CAM-specific monoclonal antibody MT201 against breast cancer cell lines," *British J. of Cancer*, 382 (2): 342-349, 2005.
Raum et al., "Anti-self antibodies selected from a human IgD heavy chain repertoire: A novel approach to generate therapeutic human antibodies against tumor-associated differentiation antigens," *Cancer Immunology and Immunotherapy*, 50 (3): 141-150, 2001.
Response to Office Communication issued in European Patent Application No. 07 703 377.7, submitted Dec. 20, 2010.
Rudikoff et al., "Single amino acid substitution altering antigen-binding specificity," *PNAS*, 79:1979, 1982.
Spizzo et al., "Prognostic significance of Ep-CAM and Her-2/neu overexpression in invasive breast cancer," *Int. J. Cancer*, 98 (6): 883-888, 2002.
Tandon et al., "Association of the 323/A3 Surface Glycoprotein with Tumor Characteristics and Behavior in Human Breast Cancer," *Cancer Res.*, 50: 3317-3324, 1990.

*Primary Examiner* — Sheela J Huff
(74) *Attorney, Agent, or Firm* — Jayme A. Huleatt

(57) ABSTRACT

The present invention relates to the use of an anti-EpCAM antibody for the manufacture of a medicament for the treatment of metastatic breast cancer. The present invention further relates to a method of treating metastatic breast cancer comprising administering said anti-EpCAM antibody.

18 Claims, 8 Drawing Sheets

Fig.1

Figure 3:
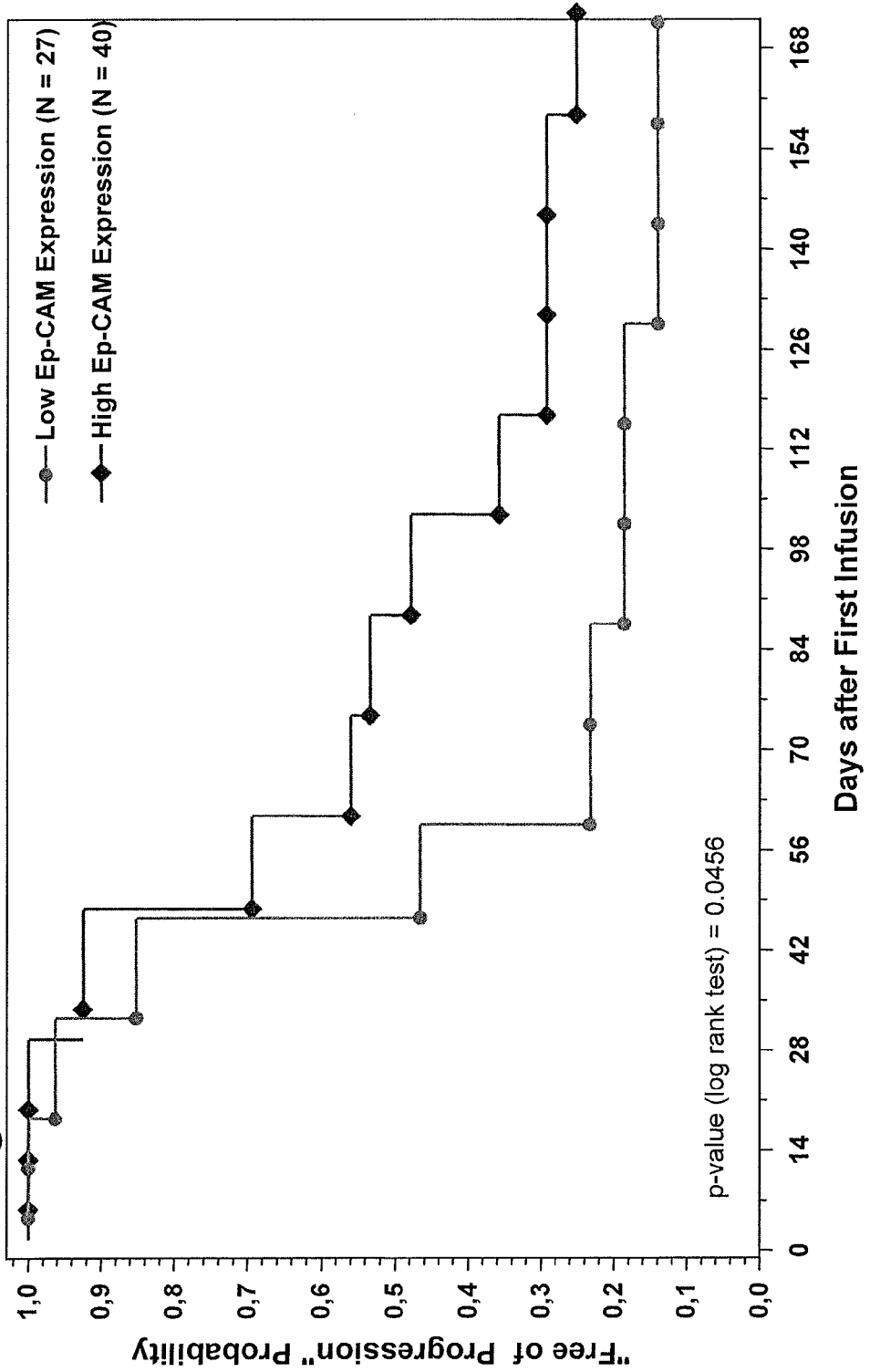

Primary Tumor (T)
T0   No evidence of primary tumor
Tis  Carcinoma in situ
T1   Tumor ≤ 2 cm
T2   Tumor > 2 cm but ≤ 5 cm
T3   Tumor > 5 cm
T4   Extension to chest wall, inflammation

Regional Lymph Nodes (N)
N0   No tumor in regional lymph nodes
N1   Metastasis to movable ipsilateral nodes
N2   Metastasis to matted or fixed ipsilateral nodes
N3   Metastasis to ipsilateral internal mammary nodes

Distant Metastasis (M)
M0   No distant metastasis
M1   Distant metastasis (includes spread to ipsilateral supraclavicular nodes)

Stage Grouping

| Stage | T | N | M |
|---|---|---|---|
| Stage 0 | Tis | N0 | M0 |
| Stage I | T1 | N0 | M0 |
| Stage IIA | T0 | N1 | M0 |
|  | T1 | N1 | M0 |
|  | T2 | N0 | M0 |
| Stage IIB | T2 | N1 | M0 |
|  | T3 | N0 | M0 |
| Stage IIIA | T0 | N2 | M0 |
|  | T1 | N2 | M0 |
|  | T2 | N2 | M0 |
|  | T3 | N1, N2 | M0 |
| Stage IIIB | T4 | N0 | M0 |
|  | T4 | N1 | M0 |
|  | T4 | N2 | M0 |
|  | Any T | N3 | M0 |
| Stage IV | Any T | Any N | M1 |

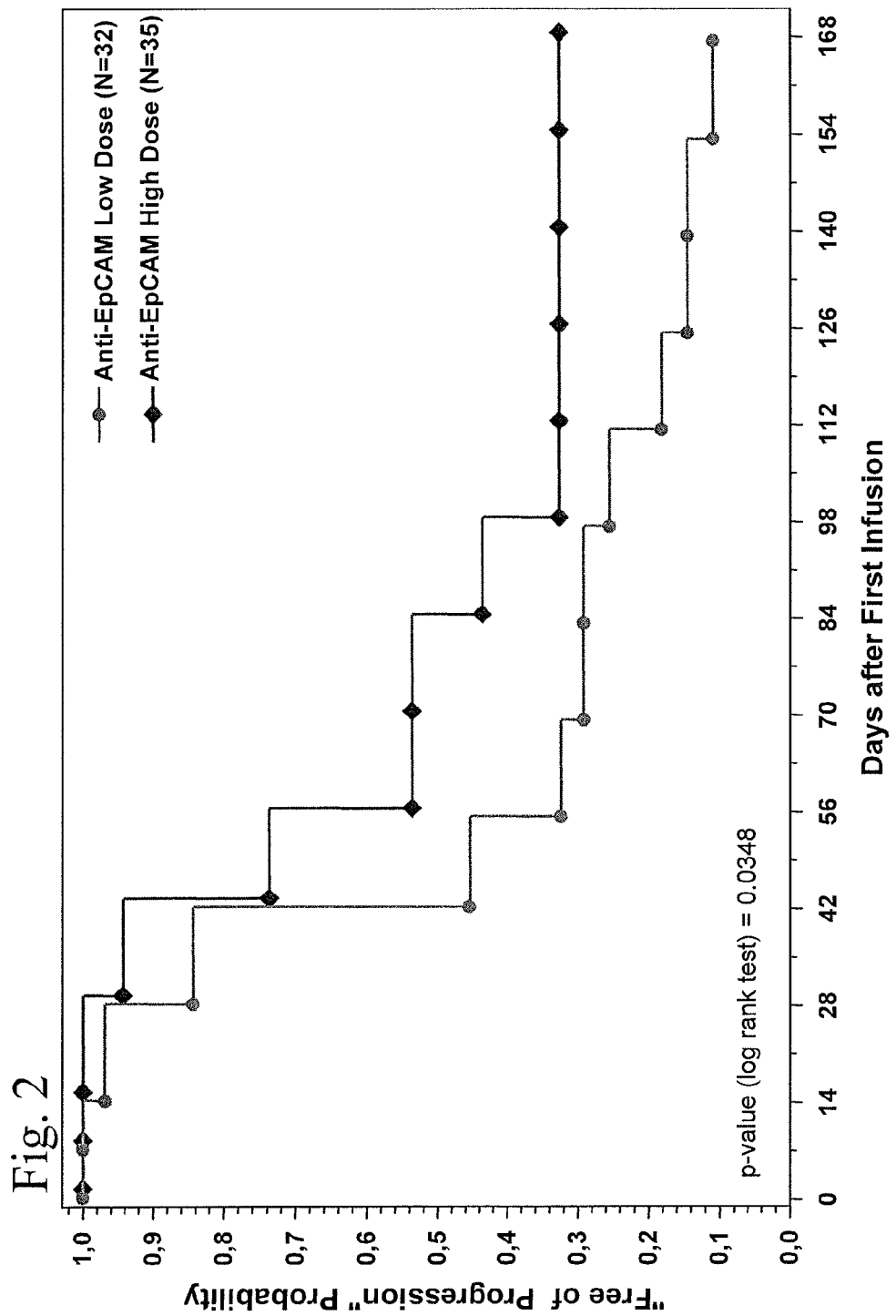

SEQUENCE LISTING

```
<160> NUMBER OF SEQ ID NOS: 8

<210> SEQ ID NO 1
<211> LENGTH: 457
<212> TYPE: PRT
<213> ORGANISM: artificial sequence
<220> FEATURE:
<223> OTHER INFORMATION: Anti-EpCAM Heavy Chain

<400> SEQUENCE: 1

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

-continued

```
                 35                  40                  45
Ala Val Ile Ser Tyr Asp Gly Ser Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Met Gly Trp Gly Ser Gly Trp Arg Pro Tyr Tyr Tyr
                100                 105                 110

Gly Met Asp Val Trp Gly Gln Gly Thr Thr Val Thr Val Ser Ser Ala
                115                 120                 125

Ser Thr Lys Gly Pro Ser Val Phe Pro Leu Ala Pro Ser Ser Lys Ser
            130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                    165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
450                 455
```

```
<210> SEQ ID NO 2
<211> LENGTH: 214
<212> TYPE: PRT
<213> ORGANISM: artificial sequence
<220> FEATURE:
<223> OTHER INFORMATION: Anti-EpCAM Light Chain

<400> SEQUENCE: 2

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 5
<212> TYPE: PRT
<213> ORGANISM: artificial sequence
<220> FEATURE:
<223> OTHER INFORMATION: Synthetic peptide

<400> SEQUENCE: 3

Ser Tyr Gly Met His
1               5

<210> SEQ ID NO 4
<211> LENGTH: 17
<212> TYPE: PRT
<213> ORGANISM: artificial sequence
<220> FEATURE:
<223> OTHER INFORMATION: Synthetic peptide

<400> SEQUENCE: 4

Val Ile Ser Tyr Asp Gly Ser Asn Lys Tyr Tyr Ala Asp Ser Val Lys
1               5                   10                  15

Gly
```

```
<210> SEQ ID NO 5
<211> LENGTH: 18
<212> TYPE: PRT
<213> ORGANISM: artificial sequence
<220> FEATURE:
<223> OTHER INFORMATION: Synthetic peptide

<400> SEQUENCE: 5

Asp Met Gly Trp Gly Ser Gly Trp Arg Pro Tyr Tyr Tyr Gly Met
1               5                   10                  15

Asp Val

<210> SEQ ID NO 6
<211> LENGTH: 11
<212> TYPE: PRT
<213> ORGANISM: artificial sequence
<220> FEATURE:
<223> OTHER INFORMATION: Synthetic peptide

<400> SEQUENCE: 6

Arg Thr Ser Gln Ser Ile Ser Ser Tyr Leu Asn
1               5                   10

<210> SEQ ID NO 7
<211> LENGTH: 7
<212> TYPE: PRT
<213> ORGANISM: artificial sequence
<220> FEATURE:
<223> OTHER INFORMATION: Synthetic peptide

<400> SEQUENCE: 7

Trp Ala Ser Thr Arg Glu Ser
1               5

<210> SEQ ID NO 8
<211> LENGTH: 9
<212> TYPE: PRT
<213> ORGANISM: artificial sequence
<220> FEATURE:
<223> OTHER INFORMATION: Synthetic peptide

<400> SEQUENCE: 8

Gln Gln Ser Tyr Asp Ile Pro Tyr Thr
1               5
```

TREATMENT OF METASTATIC BREAST CANCER

This application is a continuation of U.S. application Ser. No. 12/162,102, filed Dec. 19, 2008, which issued as U.S. Pat. No. 7,976,842 on Jul. 12, 2011, which is a national phase application under 35 U.S.C. §371 of International Application No. PCT/EP2007/001127 filed Feb. 9, 2007, which claims priority to European Patent Application No. EP 06 002 680.4 filed on Feb. 9, 2006 and U.S. Provisional Patent Application No. 60/772,421 filed Feb. 9, 2006. The entire text of each of the above-referenced disclosures is specifically incorporated herein by reference without disclaimer.

The present invention relates to the use of an anti-EpCAM antibody for the manufacture of a medicament for the treatment of metastatic breast cancer. The present invention further relates to a method of treating metastatic breast cancer comprising administering said anti-EpCAM antibody.

Breast cancer is the most common cancer and the second cause of cancer death in women. In 2001, the incidence rates of breast cancer were 90-100/100,000 in the United States and 50-70/100,000 in Europe. The incidence of the disease is growing worldwide. Risk factors for breast cancer include race, age, and mutations in the tumor suppressor genes BRCA-1 and -2 and p53. Alcohol consumption, fat-rich diet, lack of exercise, exogenous post-menopausal hormones and ionizing radiation also increase the risk of developing breast cancer. Estrogen receptor and progesterone receptor negative breast cancer ("ER-" and "PR-", respectively), large tumor size, high grade cytology and age below 35 years are associated with a bad prognosis (Goldhirsch et al. (2001). J. Clin. Oncol. 19: 3817-27). In 2005 an estimated 212,000 new cases of invasive and 58,000 new cases of non-invasive breast cancer will be diagnosed, with 40,000 women expected to die from breast cancer.

Breast cancer may generally be divided into several main stages: early, locally advanced, locally recurrent and metastatic. Early breast cancer includes non-invasive breast cancer, for example lobular carcinoma in situ ("LCIS") and ductile carcinoma in situ ("DCIS"). Most commonly, breast cancer is staged according to the Tumor Node Metastasis ("TNM") classification system proposed by the American Joint Committee on Cancer (AJCC Cancer Staging Manual, $6^{th}$ Edition). The TNM classification system defines 7 separate stages of breast cancer: 0, I, IIA, IIB, IIIA, IIIB and IV. Stages 0, I and subtypes of stage II are generally associated with early stage breast cancer. Stage III as well as subtypes of stage II are generally associated with advanced breast cancer. Stage IV is generally associated with metastatic breast cancer. More detailed information on the TNM classification of breast cancer is shown in FIG. 1. Tumor size may be measured and monitored by the Response Evaluation Criteria in Solid Tumors ("RECIST") criteria (Therasse et al. (2000). J. Natl. Cancer Inst. 92: 205-16).

While the 5-year survival prognosis for early stage breast cancer is generally above 60%, this number drops to between 40-60% for advanced breast cancer. The 5-year survival prognosis is generally around 15% for metastatic breast cancer. The most common sites of distant metastasis for breast cancer include lung, liver, bone, lymph nodes, skin and CNS (brain). Once metastatic breast cancer has been diagnosed, a patient may on average expect to live a further 18-24 months. Cure for metastatic breast cancer is unlikely, and the modes of therapy for this systemic disease are largely palliative in nature.

The above emphasizes the importance of new developments in breast cancer therapy, especially therapy for metastatic breast cancer.

Current therapeutic options for treatment of breast cancer, including metastatic breast cancer, include surgery (e.g. resection, autologous bone marrow transplantation), radiation therapy, chemotherapy (e.g. anthracyclines such as doxorubicin, alkylating agents such as cyclophosphamide and mitomycin C, taxanes such as paclitaxel and docetaxel, anti-metabolites such as capecitabine, microtubule inhibitors such as the vinca alkaloid navelbine), endocrine therapy (e.g. anti-estrogens such as tamoxifen, progestins such as medroxyprogesterone acetate and megastrol acetate, aromatase inhibitors such as aminoglutethamide and letrozole) and biologics (e.g. cytokines, immunotherapeutics such as monoclonal antibodies). Most commonly metastatic breast cancer is treated by one or a combination of chemotherapy (the most effective drugs including cyclophosphamide, doxorubicin, navelbine, capecitabine and mitomycin C) and endocrine therapy.

The standard care in breast cancer is surgical removal of the tumor and radiotherapy, preceded or followed by either hormonal therapy or chemotherapy, depending on the tumor stage and risk factors. Patients with stage I to stage IIIA (see below, as well as FIG. 1) may be treated with adjuvant chemotherapy or hormone therapy. In patients with inoperable invasive stage IIIB disease or stage IV metastatic breast cancer, chemotherapy merely alleviates the symptoms.

Recently taxanes and anthracyclines have markedly improved the survival rates of breast cancer patients. Capecitabine (Xeloda®, capecitabine, Roche Ltd: Summary of Product Characteristics) has been approved for second-line or higher treatment in patients who have failed cytotoxic chemotherapy including anthracyclines and/or taxanes, especially because of its low toxicity and oral formulation (O'Shaughnessy (2002). Oncology 16: 17-22). However, despite these improved treatment modalities, survival of patients with advanced breast cancer remains poor and chemotherapy is only palliative.

The monoclonal anti-Her-2/neu antibody trastuzumab (Herceptin®, trastuzumab, Roche, Ltd: Summary of Product Characteristics, March 2002) was the first biological targeted therapy approved for treatment of patients with breast cancer whose tumors overexpress Her-2/neu. In combination with paclitaxel, it is indicated as a first-line treatment of patients with metastatic breast cancer and as second-line or higher treatment as single agent in the same patient population(Cardoso et al. (2002). Clin. Breast Cancer 3: 258-9; Tan-Chiu & Piccart (2002). Oncology 63: 57-63). However, only a small fraction of patients with breast cancer (approximately 20%) overexpress Her2/neu at a high level, and are therefore eligible for treatment with this antibody.

Therefore, development of new anti-cancer drugs, especially for the treatment of breast cancer patients in whom trastuzumab is not indicated, is an important medical need.

One promising immunotherapeutic is the human antibody comprising in its heavy chain variable region amino acid sequences as set out in SEQ ID NOs. 3, 4 and 5, and/or comprising in its light chain variable region amino acid sequences as set out in SEQ ID NOs. 6, 7 and 8. Hereinafter this antibody will be referred to as "Anti-EpCAM", and is further characterized in its heavy and light chains by the amino acid sequences as set out in SEQ ID NOs. 1 and 2, respectively). This antibody binds to the epithelial cell adhesion molecule ("EpCAM", also called 17-1A antigen, KSA, EGP40, GA733-2, ks 1-4 and esa). EpCAM is a highly conserved surface glycoprotein which is overexpressed in many carcinomas of different origins, including breast cancer. Tumor samples from 3722 patients with colon, stomach, lung, ovarian or prostate cancer were analyzed for EpCAM expression using a sensitive immunohistochemical staining assay on tissue microarrays. An intermediate to strong EpCAM expression was reported in more than 88% of all tumor samples, in 94% of ovarian cancers, 94% of colon cancers, 92% of stomach cancers, 90% of prostate cancers and in 71% of lung cancers. These results confirm that EpCAM is frequently present in epithelial tumor cells, and highlights Anti-EpCAM as a potential diagnostic and therapeutic target.

In two studies in primary breast cancer tumors, strong EpCAM expression was shown in 36% of 384 sections (Tandon et al. (1990) Cancer Res. 50: 3317-24) and 59% of 128 samples (Edwards et al. (1986) Cancer Res. 46: 1306-17), respectively. In another study (Spizzo et al. (2002) Int. J. Cancer 98: 883-8), strong EpCAM expression was found in 73 of 205 (36%) primary breast tumor specimens and the authors report that EpCAM overexpression in breast cancer was associated with reduced disease-free and overall survival. EpCAM overexpression was also correlated with tumor size and with hormone receptor negativity; it was highest in ductal breast cancers as well as in histological grade III subtypes. In another series, approximately 90% of breast cancer samples were shown to express EpCAM to some extent and more than 40% showed strong EpCAM expression.

In vitro, Anti-EpCAM causes both antibody-dependent cellular cytotoxicity ("ADCC") and complement-dependent cytotoxicity ("CDC"). As the most likely mechanism of action, Anti-EpCAM recruits the patient's natural killer cells to the tumor site by binding to EpCAM-positive tumor cells. Via activation of the patient's immune effector cells, EpCAM-positive tumor cells can then be eliminated.

Certain therapeutic regimens employing Anti-EpCAM are known in the art (WO 2005/080428). Specifically, WO 2005/080428 describes a therapeutic regimen involving administration of Anti-EpCAM to cancer patients. Here, it was contemplated to administer Anti-EpCAM in the treatment of for example, breast cancer or a minimal residual disease. In the context of the latter, a minimal residual disease may be understood as the local and non-local reoccurrence of a tumor caused by the survival of single tumor cells.

It is a goal of the present invention to improve upon existing breast cancer therapies.

Accordingly, one aspect of the invention relates to a use of an anti-EpCAM antibody comprising amino acid sequences as set out in SEQ ID NOs. 3, 4, 5, 6, 7 and/or 8 ("Anti-EpCAM"), for the manufacture of a medicament for the treatment of human metastatic breast cancer.

As used herein, the term "metastatic breast cancer" is to be understood as a disease in which at least one transformed, i.e. cancerous cell from a primary tumor of the breast has become separated from the primary tumor and has continued to grow into a tumor at a location distinct from that of the primary tumor (hereinafter "distinct location"). The distinct location may for example be within the same breast as that in which the primary tumor is located (ipsilateral breast) or within the other breast (contralateral breast). As further examples, the distinct location may be within one or more lymph nodes, whether these are movable or fixed, ipsilateral or contralateral to the primary tumor, supraclavicular, axillary or otherwise. Within the context of the TNM tumor classification system (shown in FIG. 1), a "metastatic breast cancer" as used herein would include i.e. all tumors whose staging includes M=1 (i.e. Stage IV breast cancer; see FIG. 1), i.e. all tumors for which any degree of metastasis exists to distant locations such as for example lung, liver, bone, lymph nodes, skin, brain and/or a distinct location within an ipsilateral and/or contralateral breast.

The term "breast cancer" as used herein denotes a disease in which a primary tumor or multiple individual primary tumors exist in the breast or breasts. Generally, this means that no cancerous cell has (yet) become separated from the primary tumor in the breast, and has not spread to a "distinct location". In this context, it should be noted that the existence of multiple primary tumors within the same or within both the ipsilateral and contralateral breasts is not in itself to be understood as falling within the meaning of "metastatic breast cancer". This is because multiple cells within one or both breasts may give rise to multiple primary tumors, none of which are or have yet become metastatic. On the other hand, the separation of a cancerous cell from only one of multiple primary tumors within a single breast and the subsequent development of this single cell at a "distinct location" into a separate tumor would constitute "metastatic breast cancer" as used herein, irrespective of the presence or absence of one or more primary tumors in at least one of the breasts.

It should be noted that the term "metastatic breast cancer" as used herein does not imply that said metastasis existing at a "distinct location" must have arisen from any one particular primary tumor of the breast. That is to say, the origin of the metastasis at the "distinct location" is immaterial to the designation of the disease as "metastatic breast cancer" as long as the primary tumor giving rise to the metastasis originated in the breast tissue. For this purpose, the term "breast tissue" is to be understood as including the lobules and the ducts of the breast, i.e. the tissue which most commonly gives rise to tumors of the breast.

The applicant has surprisingly found that Anti-EpCAM is well suited not only to the treatment of breast cancer as such, i.e. breast cancer involving at least one primary tumor in the breast, but also to the treatment of metastatic breast cancer. That Anti-EpCAM can be used in this fashion is not at all to be expected, as the tumor load (i.e. the number of cancer cells, the size of a tumor, or the amount of cancer in the body; also called "tumor burden") associated with metastatic breast cancer is generally greater than that observed in non-metastatic breast cancer. This is because a single primary breast tumor may well—and often does—engender multiple dispersed metastases throughout the body. The absolute number of EpCAM molecules existing on the surface of malignant cells throughout the body is therefore generally greater in metastatic breast cancer than in non-metastatic breast cancer. The data provided in the appended examples show that the administration of a pharmaceutical composition comprising an anti-EpCAM antibody leads to a significant prolongation of the TTP (time to progression) of the treated disease. The actual effect appears to be correlated with the expression level of EpCAM on the surface of the malignant cells to be treated. Patients may be sorted into groups of different groups of EpCAM expressors according to Gastl et al. (2000) Lancet 356, 1981-2. Briefly, Gastl et al. analyzed the EpCAM expression of tumor cells isolated from different patients in immunohistochemical stains. A total immunostaining score was calculated as the product of a proportion score and an intensity score. The proportion score describes according to Gastl et al. the estimated fraction of positive-stained tumor cells (0, none; 1, <10%; <10%; 2, 10%-50%; 3, 50%-80%; 4, >80%). The intensity score represented according to Gastl et al. the estimated staining intensity (0, no staining; 1, weak; 2, moderate; 3, strong). The resulting total score ranges from 0 to 12. High EpCAM is defined as a total score greater than 4, since the patient sample showed a bimodal distribution of EpCAM expression (low and high EpCAM expressors) with the discriminating nadir at a total score value of 3 to 4. The prognosis for a patient receiving a therapy comprising the administration of an anti-EpCAM antibody, which is identified as a high EpCAM expressor is more optimistic than for a patient identified as a moderate or low EpCAM expressor. In line with this observation patients identified as extremely high EpCAM expressors (a patient showing a higher amount of EpCAM on the surface of malignant cells than the mean of high EpCAM expressors, i.e. a total score of $\geq 8$) show a further prolongation of the TTP compared with the patients identified as high EpCAM expressors and receiving the same therapy. Moreover, the amount of anti-EpCAM antibody in a pharmaceutical composition administered to a patient directly correlates with the prognosis. In particular, the administration of high dose of anti-EpCAM antibody results in a prolongation of the TTP of the treated disease compared to the administration of a low dose to a patient of the same group of EpCAM expressors.

In one preferred embodiment the anti-EpCAM antibody Anti-EpCAM is a human antibody.

In a further preferred embodiment Anti-EpCAM comprises all of SEQ ID NOs. 3, 4, 5, 6, 7 and 8. In a further preferred embodiment, Anti-EpCAM comprises SEQ ID NOs. 1 and/or 2. In an especially preferred embodiment, Anti-EpCAM comprises both SEQ ID NOs. 1 and 2.

According to a preferred embodiment, the treatment of metastatic breast cancer comprises long-term stabilization of metastatic breast cancer. "Long-term stabilization" is to be understood as the case in which disease progression is stabilized at or below its beginning level over the course of treatment with the anti-EpCAM antibody. This may be understood as a prolongation of the time taken to disease progression. "Long-term stabilization" also comprises the scenario in which the tumor shrinks (partial response). "Long-term stabilization" also comprises the scenario in which disease progression is reduced to or below the detectable level, i.e. the patient responds completely to treatment and the disease is cured (complete response). In such a scenario, treatment may be continued indefinitely as needed to prevent recurrence of the disease, or may be terminated at the physician's discretion.

According to a preferred embodiment, the medicament is suitable for a so-called "low dose administration". For the low dose administration the dose of each administration is in a range of 1 to 3 mg anti-EpCAM antibody/kg body weight. Preferably, the low dose administration comprises at least one loading dose in a range of 1 to 3 mg/kg body weight, followed by multiple maintenance doses, each maintenance dose being in a range of 1 to 3 mg/kg body weight. It is also preferred that the individual doses for the low dose administration are in a range of 1.5 to 2.5 mg/kg body weight, more preferably, in a range of 1.75 to 2.25 mg/kg body weight. Most preferably, the individual doses for the low dose administration is 2 mg/kg body weight. It is preferred for the low dose administration that the at least one loading dose for the low dose administration is of 2 mg/kg body weight followed by multiple maintenance doses, each maintenance dose being 2 mg/kg body weight. Alternatively, the medicament is suitable for a so-called "high dose administration". For the high dose administration the dose of each administration is in a range of 4.5 to 8 mg anti-EpCAM antibody/kg body weight. Preferably, the high dose administration comprises at least one loading dose in a range of 4.5 to 8 mg/kg body weight, followed by multiple maintenance doses, each maintenance dose being in a range of 4.5 to 8 mg/kg body weight. It is also preferred that the individual doses for the high dose administration are in a range of 5 to 7 mg/kg body weight, more preferably, in a range of 5.5 to 6.5 mg/kg body weight, further preferably, in a range of 5.75 to 6.25 mg/kg body weight. Most preferably, the individual doses for the high dose administration is 6 mg/kg body weight. It is preferred for the high dose administration that the at least one loading dose for the high dose administration is of 6 mg/kg body weight followed by multiple maintenance doses, each maintenance dose being 6 mg/kg body weight. It is unexpected that such loading and maintenance doses would yield a therapeutic benefit for the treatment of metastatic breast cancer, in which multiple metastases throughout the body are to be eradicated.

According to a further embodiment of the invention, it may be advantageous to establish whether a metastatic breast cancer patient expresses EpCAM to a higher or to a lower extent. Patients may be sorted into groups of non-EpCAM expressors, moderate EpCAM expressors, low EpCAM expressors and high EpCAM expressors as for example described in Gastl et al. (2000) Lancet 356, 1981-2. In general, it can be advantageous to correlate the amount of Anti-EpCAM administered to a metastatic breast cancer patient with the level of EpCAM expression observed for the patient in question, with high EpCAM expressors receiving higher doses of Anti-EpCAM and low EpCAM expressors receiving lower doses of Anti-EpCAM. It can be especially advantageous to administer to patients expressing high levels of EpCAM the higher of the two above doses of Anti-EpCAM, namely 6 mg/kg body weight.

According to a further embodiment of the invention, the duration of time between a respective loading dose and either another successive loading dose or a first maintenance dose is to be no longer than a week, while the duration of time between a respective maintenance dose and a following maintenance dose is to be no longer than two weeks. Preferably, the/each loading dose/s is/are administered every week and each of said maintenance doses is administered every second week. Weekly administration of loading doses of Anti-EpCAM in the "loading phase" ensures that the minimum level of Anti-EpCAM in serum (taking account of continual clearance in the form of excretion and elimination) remains high enough at all times to elicit the desired therapeutic effect. This minimum level of Anti-EpCAM required for therapeutic effect is known as the "serum trough level", and will be referred to as such hereinbelow. Once this serum level is reached, further administration of maintenance doses of Anti-EpCAM in the subsequent "maintenance phase" in two-week intervals ensures (again, taking account of continual clearance) that the serum level of Anti-EpCAM never sinks below what is required for a continued therapeutic effect. The pharmacokinetic calculations required to determine the serum trough level for Anti-EpCAM are described in the art (see WO 2005/080428).

According to an especially preferred embodiment, one loading dose is administered at the beginning of each of therapy weeks 1, 2 and 3 followed by 11 maintenance doses, one maintenance dose being administered at the beginning of each of therapy weeks 4, 6, 8, 10, 12, 14, 16, 18, 20, 22 and 24. Here, it has been surprisingly found that the combination of 3 loading doses in the above time intervals followed by 11 maintenance doses in the above intervals is especially effective in treating metastatic breast cancer. This implies a total therapeutic period of 24 weeks from start to finish (not taking into account any post-treatment checkups normally associated with any kind of such therapies). In a further preferred embodiment the total therapeutic period from start to finish is of 30 weeks, 40 weeks, 50 weeks or 60 weeks. It is also preferred that a period of administration of EpCAM antibody in line with the above described scheme is followed by a period without administration of EpCAM antibody and a further therapeutic period of administration of EpCAM antibody. Such an order of periods may be repeated for several times.

Alternatively, a further embodiment of the invention contemplates administration of Anti-EpCAM in loading doses as described above, followed by as many maintenance doses as required to control tumor progression. Within this embodiment, tumor progression may be seen as being controlled as long as the size of one or more monitored metastatic tumors is not increasing. In the best case, the size of one or more tumors monitored may actually shrink (as in a partial response). Here, the tumor(s) monitored may shrink to nothing, i.e. may disappear (as in a complete response). The tumor(s) monitored may remain the same size and the time to disease progression may thus be increased (as in stabilized disease). According to this embodiment, therefore, maintenance doses of Anti-EpCAM may be continued in the above intervals indefinitely as long as there is either a partial response or a stable response, continuing to the case in which a complete response is measured. In the case of further tumor progression (i.e. the size or number of the monitored tumor(s) increases during treatment), the treatment with Anti-EpCAM may be terminated and, if appropriate, be replaced by an alternate form of therapy.

According to a further embodiment of the invention, Anti-EpCAM is administered as a solution comprising 0.9% sodium chloride.

According to a further embodiment of the invention, Anti-EpCAM is administered to a metastatic breast cancer patient intravenously.

A further aspect of the invention is the use of Anti-EpCAM for the treatment of metastatic breast cancer.

A further aspect of the invention relates to a method of treating human metastatic breast cancer, said method comprising administering to a human an anti-EpCAM antibody comprising SEQ ID NOs. 3, 4, 5, 6, 7 and/or 8. This antibody is further characterized by heavy and light chains amino acid sequences as set out in SEQ ID NOs. 1 and 2, respectively. Preferred embodiments of the present method of treating metastatic breast cancer are as set out above in the context of the inventive use; these embodiments apply to the present inventive method mutatis mutandi.

The invention will now be illustrated by the following figures and non-limiting examples.

BRIEF FIGURE LEGENDS

FIG. 1 Overview of the TNM Classification/Staging System for breast cancer

Figure 4:
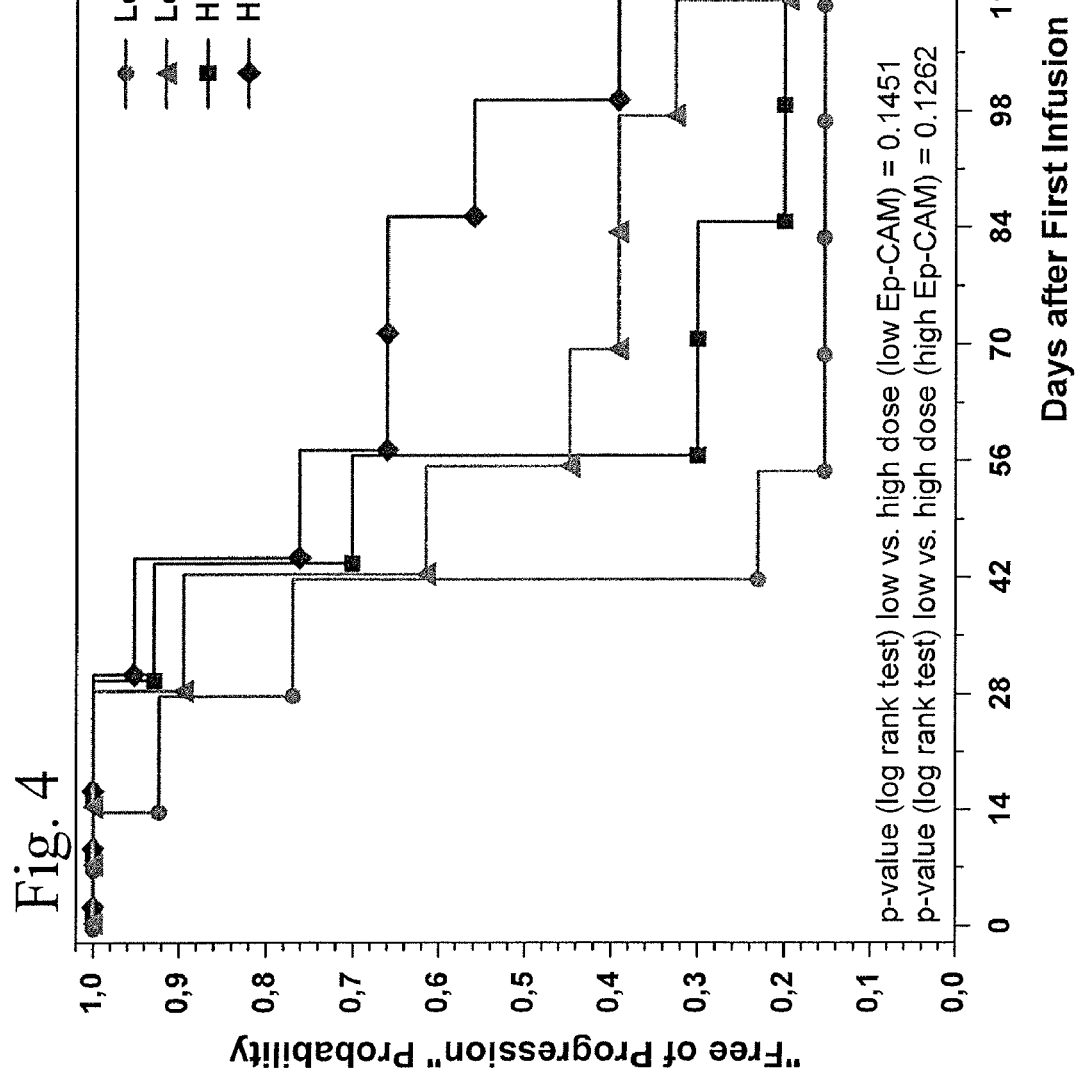
Figure 5:
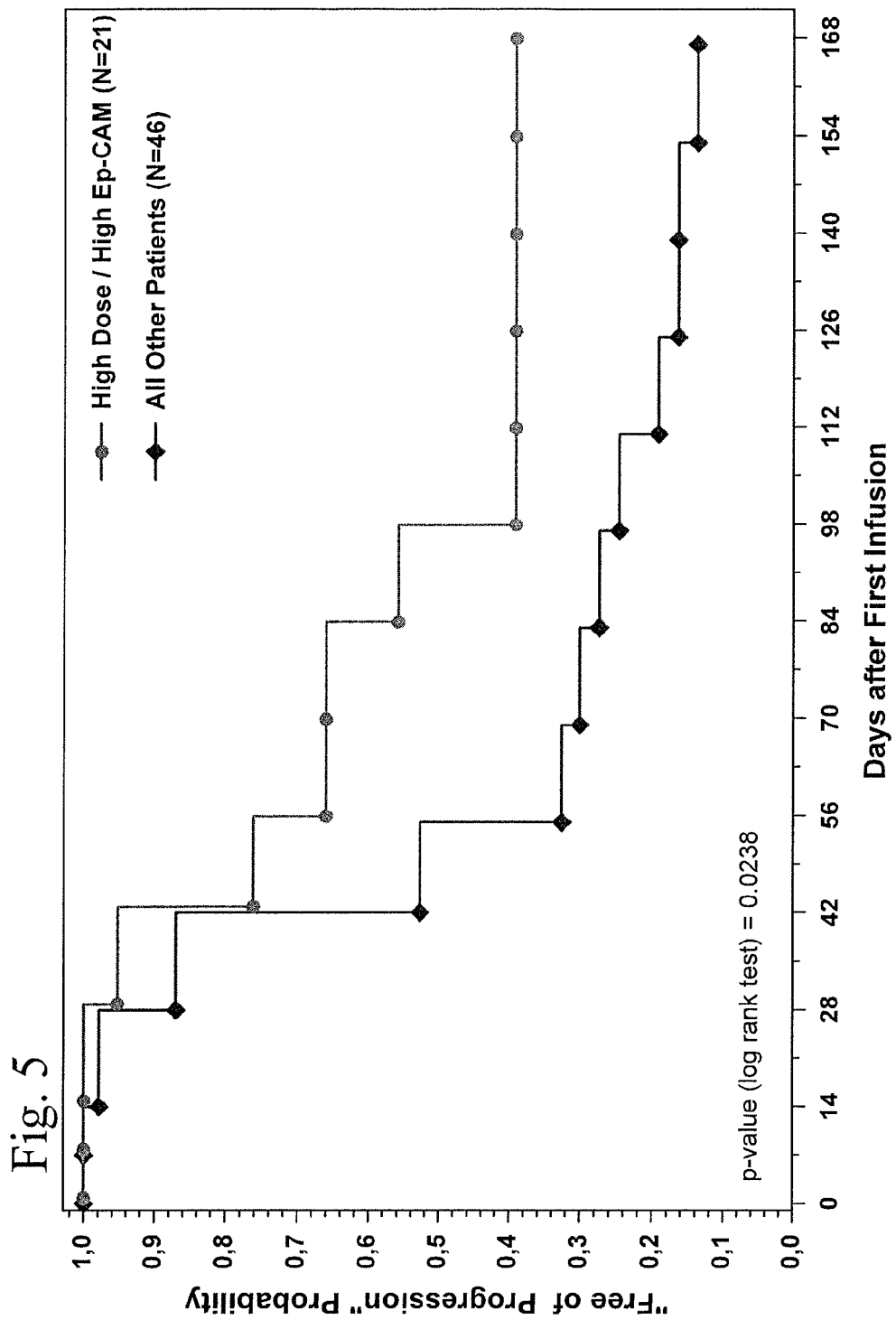

FIG. 2 Time To Progression ("TTP") plot showing the probability of being free of disease progression vs. time for low and high administered doses of Anti-EpCAM to 32 and 35 patients, respectively FIG. 3 ("TTP") plot showing the probability of being free of disease progression vs. time for low and high administered doses of Anti-EpCAM to 27 and 40 patients, respectively FIG. 4 ("TTP") plot showing the probability of being free of disease progression vs. time for high and low doses of Anti-EpCAM administered to patients expressing both high and low levels of EpCAM FIG. 5 ("TTP") plot showing the probability of being free of disease progression vs. time for high doses of Anti-EpCAM administered to patients expressing high levels of EpCAM, as compared to all other patients.

Figure 6:
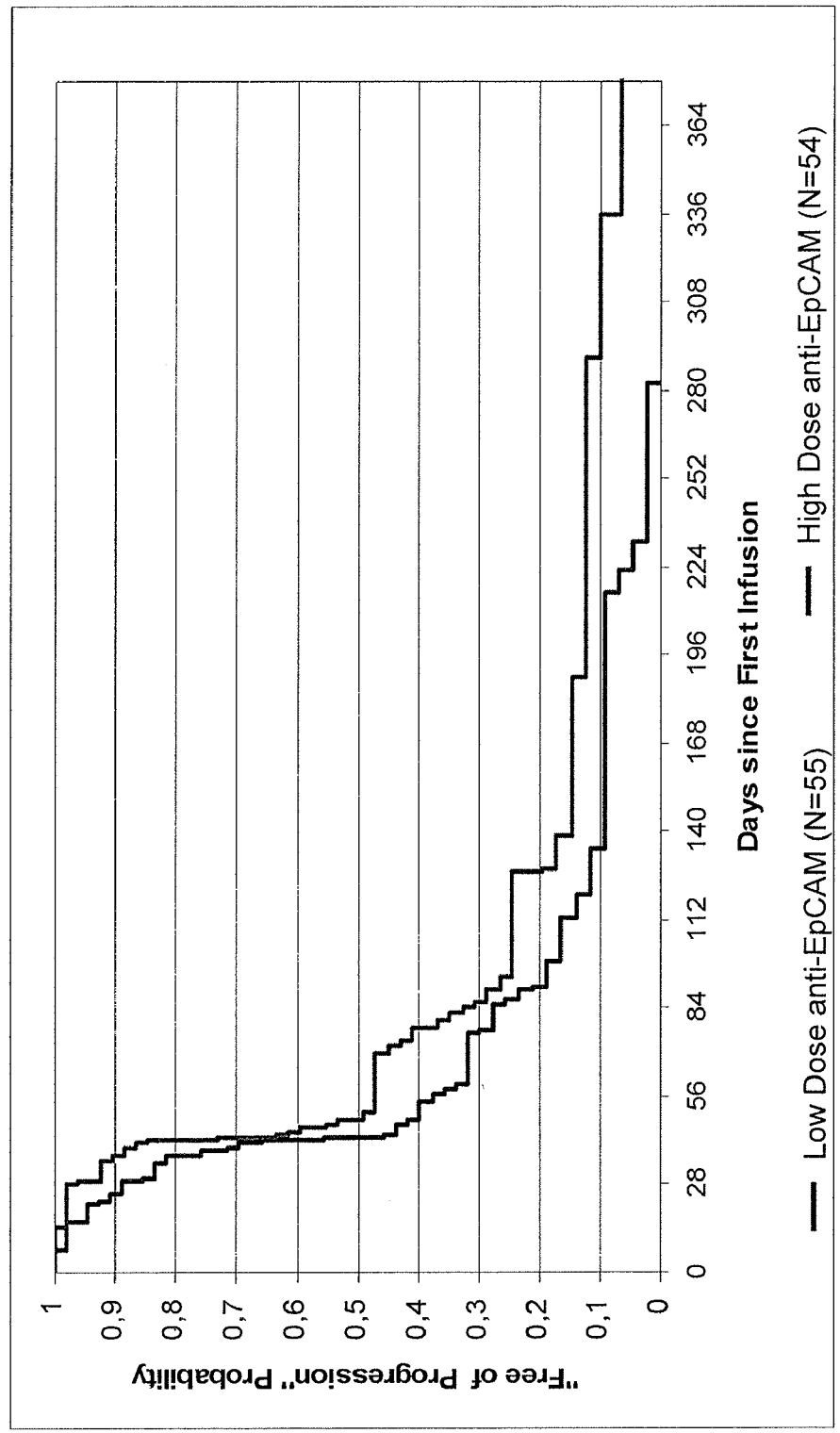
Figure 7:
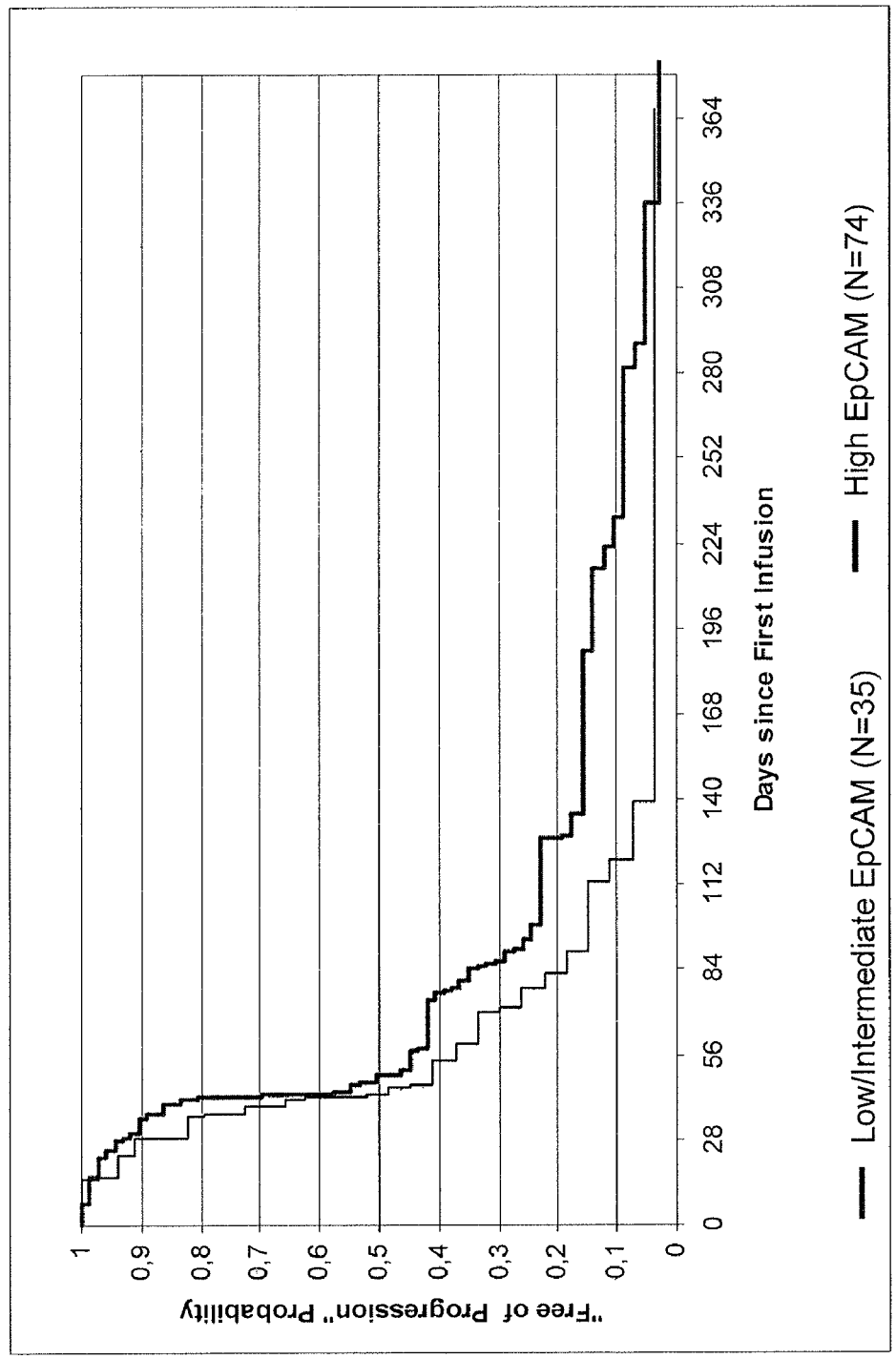
Figure 8:
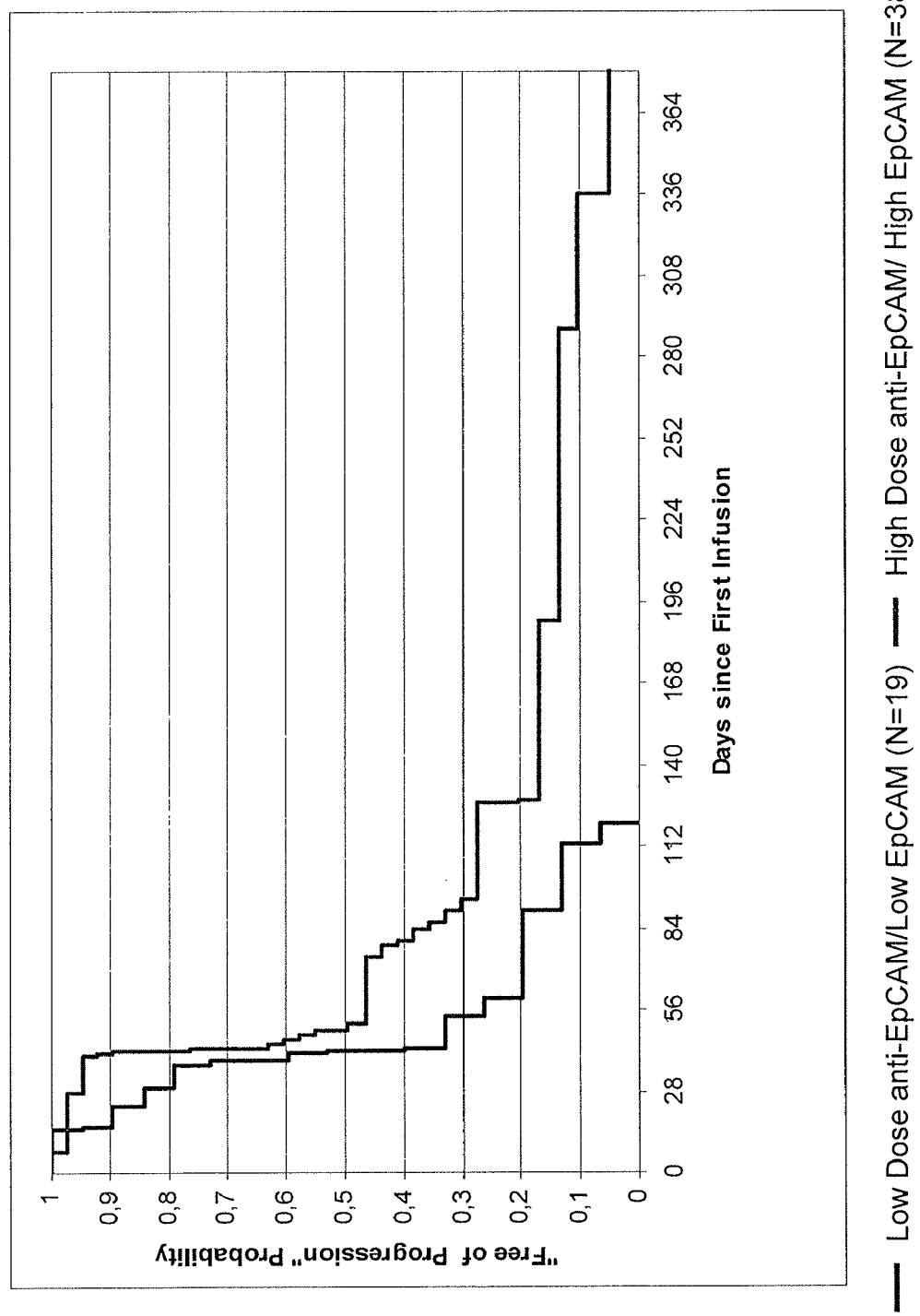

FIG. 6 ("TTP") plot showing the probability of being free of disease progression vs. time for low and high administered doses of Anti-EpCAM to 54 and 55 patients, respectively FIG. 7 ("TTP") plot showing the probability of being free of disease progression vs. time for high and low doses of Anti-EpCAM administered to patients expressing both high and low levels of EpCAM FIG. 8 ("TTP") plot showing the probability of being free of disease progression vs. time for high doses of Anti-EpCAM administered to patients expressing high levels of EpCAM, as compared to low doses of Anti-EpCAM administered to patients expressing low levels of EpCAM.

EXAMPLES

General

The following examples are intended to illustrate various aspects of the invention and are in no way limiting to the invention's scope. Generally, the examples describe a clinical study program designed for the fully human IgG1 antibody termed "Anti-EpCAM" as well as results from this clinical study program. The amino acid sequences of the first, second and third complementarity determining regions (CDRs) of the heavy chain variable region of Anti-EpCAM are as set out in SEQ ID NOs. 3, 4 and 5, respectively. The amino acid sequences of the first, second and third CDRs of the light chain variable region of Anti-EpCAM are as set out in SEQ ID NOs. 6, 7 and 8, respectively. The amino acid sequence of the heavy chain of Anti-EpCAM is as set out in SEQ ID NO. 1 and the amino acid sequence of the light chain of Anti-EpCAM is as set out in SEQ ID NO. 2. Throughout the following examples, the following terms and abbreviations are used:

| | |
|---|---|
| ADCC | antibody-dependent cell-mediated cytotoxicity |
| AE | adverse event |
| ALT | alanine aminotransferase |
| ANCOVA | analysis of covariance |
| AP | alkaline phosphatase |
| AST | aspartate aminotransferase |
| AUC | area-under-the-curve |
| BRCA | breast cancer tumor suppressor gene |
| CBA | cytometric bead array |
| CDC | complement-dependent cytotoxicity |
| CHO | Chinese hamster ovary |
| $C_{min}$ | minimum drug concentration |
| CNS | central nervous system |
| CR | complete Response |
| CRF | case report form |
| CRP | C-reactive protein |
| CT | computerized tomography |
| CTCAE | common terminology criteria for adverse events |
| ECOG | Eastern Cooperative Oncology Group |
| ELISA | enzyme-linked immunosorbent assay |
| EpCAM | epithelial cell adhesion molecule |
| FAS | full analysis set |
| GCP | good clinical practice |
| GGT | gamma-glutamyltransferase |
| HAHA | human anti-human antibodies |
| HBsAg | hepatitis B surface antigen |
| HCV | hepatitis C virus |
| HIV | human immunodeficiency virus |
| ICF | informed consent form |
| IEC | independent ethics committee |
| INR | international normalized ratio |
| IRB | institutional review board |
| LDH | lactic dehydrogenase |
| NK | natural killer |
| OTR | overall tumor response |
| PK | pharmacokinetic |
| PP | per protocol analysis set |
| PR | partial response |
| PT | prothrombin time |

| | |
|---|---|
| PTT | partial thromboplastin time |
| PVP | polyvinylpyrrolidone |
| RBC | red blood cell |
| RECIST | Response Evaluation Criteria in Solid Tumors |
| SAE | serious adverse event |
| SAF | safety analysis set |
| SAP | statistical analysis plan |
| SD | stable disease |
| SGOT | serum glutamic oxaloacetic transaminase |
| SGPT | serum glutamic pyruvic transaminase |
| ULN | upper limits of normal |
| WBC | white blood cell |
| WHO | World Health Organization |

Example 1

Phase II Clinical Study Program Designed for Anti-EpCAM

Example 1.1

Summary of Clinical Study

The clinical study designed for Anti-EpCAM is summarized in the following table (Table 1).

TABLE 1

| Clinical Study Summary | |
|---|---|
| Study Rationale | Anti-EpCAM is a novel, fully human IgG1 monoclonal antibody, derived from the repertoire of human IgD-positive B cells, binding specifically to the epithelial cell adhesion molecule (EpCAM). EpCAM is a highly conserved surface glycoprotein, which is overexpressed in many carcinomas of different origin, including breast cancer. Anti-EpCAM has been shown to effectively kill breast tumor cells by antibody-dependent cellular cytotoxicity (ADCC) in preclinical experiments and to be safe in humans.<br>This study will investigate whether Anti-EpCAM has anti-tumor activity in patients with metastatic breast cancer and if it could offer a novel treatment option for these patients. |
| Study Design | A randomized, open-label, multicenter, parallel group, phase II study.<br>The study is designed to evaluate the efficacy and safety of Anti-EpCAM over 24 weeks of therapy at two different doses with positive EpCAM testing. The central randomization process will be stratified according to the EpCAM test results performed at screening. Upon registration in one of the EpCAM strata, patients will be randomly assigned to either the low dose treatment group or the high dose treatment group. |
| Concomitant Medication | Prohibited:<br>Any concomitant anti-tumor therapy other than the investigational product Anti-EpCAM such as hormonal therapy, biological therapy, chemotherapy, radiation therapy.<br>Therapy with chronic systemic high-dose corticosteroids and other immunosuppressive drugs.<br>Any other investigational agent. |
| Duration of Patient Participation/ Duration of the Study | For each patient, the study consists of a 4-week screening period, a 24-week treatment period and a 4-week safety follow-up period and a final PK/PD visit (12 weeks after end of therapy).<br>The estimated accrual period is 9 months and the total duration of the study is expected to be 22 months. |
| Measurements and Evaluation | Each patient will have a maximum of 18 visits, including one screening visit, 14 visits during the treatment period, and one final PK/PD Assessment 12 weeks after the end of therapy.<br>Patients may also undergo unscheduled visits in case of changes in their medical condition. |
| Efficacy | Efficacy evaluations will occur every 6 weeks after the first administration of Anti-EpCAM until week 24 and every 8 weeks thereafter (during follow-up study), and will include the following:<br>Thoracic CT scan or chest X-ray<br>Abdominal CT scan or MRI<br>Bone scintigraphy (for patients with bone metastasis at screening)<br>Responses must be confirmed at a follow-up evaluation not earlier than 4 weeks later. |
| Safety | A physical examination or a symptom-directed examination, including vital signs, and laboratory parameters (hematology, clinical chemistry, coagulation profile, and urinalysis) will be conducted at every visit, except visit 18.<br>ECG will be performed at screening.<br>ECOG performance status will be assessed at screening.<br>Samples for Immunogenicity analysis (HAHA) will be taken at screening. |
| Pharmacodynamics | Blood samples for measurement of natural killer (NK) cells will be collected at visits 2, 3 and 15. |
| Pharmacokinetics | Anti-EpCAM serum trough and peak levels will be measured at visits 2 to 6, during the treatment period every 6 to 8 weeks and at the follow-up visits 16 to 18. |
| Statistical Methods | Sample size:<br>According to sample size calculations based on Fleming's standard single-stage procedure but using the exact binomial distribution (A'Hern), 24 patients evaluable for efficacy are required per treatment arm to provide a 85% chance (i.e. power = 80%) of demonstrating that the 95% one-sided confidence interval (i.e. type one error = 5%) for the response rate excludes 5% if the true |

TABLE 1-continued

Clinical Study Summary clinical benefit rate is 25%. Assuming that approximately 10% of the patients will not be evaluable with regard to efficacy (drop-outs), a total of at least 108 patients (27 per treatment arm) should be randomized in the study.
Statistical analysis:
The primary analysis will be based on the full analysis set.
In a first step, the clinical benefit rate (patients with stable disease $\geq$ 24 weeks + CR + PR according to RECIST (see Example 1.18)) in each of the four treatment arms will be evaluated separately. A 95% one-sided confidence interval will be calculated for the clinical benefit rate in each treatment arm. If the lower bound of the 95% one-sided confidence interval of the response rate is larger than $p_0 = 5\%$ in a treatment arm, the null hypothesis will be rejected for this treatment arm. The cut-off point in this study is 4; meaning that as soon as 4 patients with clinical benefit have been achieved in a treatment arm the null hypothesis for the respective treatment can be rejected.
If all treatment arms show sufficient activity, the treatment arms with the same dose level will be pooled and the dose levels will be compared allowing for unequal clinical benefits rates of patients with low/moderate EpCAM expression or patients with high EpCAM expression. The comparison of the two dose levels will be conducted by means of a logistic regression model with the two factors, EpCAM expression and dose level, out of which the appropriate odds ratios for the two dose levels will be calculated.
If both dose levels show sufficient activity only in one of the patient populations (either patients with low/moderate EpCAM expression or high EpCAM expression), these two dose levels will be compared descriptively.
All secondary endpoints (efficacy and safety) will be analyzed descriptively.

Example 1.2

Summary Of Non-Clinical Studies With Anti-EpCAM

The efficacy of Anti-EpCAM and trastuzumab to induce ADCC was studied using nine breast cancer cell lines. Anti-EpCAM was capable of mediating ADCC specific lysis to the same levels as trastuzumab. There was a strong correlation between the concentration of EpCAM molecules on the cell surface and the susceptibility to ADCC using Anti-EpCAM. In all cases, maximal specific lysis was achieved at Anti-EpCAM concentrations below 10 µg/mL, which is the minimal trough concentration targeted in patients.

Anti-EpCAM showed an excellent local tolerance in rabbits at the intended intravenous route of administration, no macroscopic and only minor microscopic changes were observed.

Example 1.3

Rationale for Dose Selection

Based on preclinical experiments, serum trough levels of 10 µg/mL are expected to be effective for anti-tumor activity of Anti-EpCAM. However, it cannot be ruled out that higher doses might be more effective. Therefore, a second dose, calculated to achieve serum trough level of 30 µg/mL, will be evaluated in this study.

The doses intended in this study do not exceed the highest doses administered to patients in the phase I study. Loading phases and maintenance phases have been calculated using pharmacokinetic modeling to achieve targeted trough serum concentrations within a short period of time and to avoid maximum plasma concentrations that would exceed the ones assessed in the phase I study.

Example 1.4

Known Benefits

Preclinical data suggest that patients with metastatic breast cancer and other tumors may benefit from a delay of progression (stable disease) by elimination of tumor cells, which express EpCAM, via Anti-EpCAM.

Example 1.5

Clinical Study Objectives

Primary Objective
  To evaluate the clinical benefit of two different doses of Anti-EpCAM in patients with EpCAM positive, metastatic breast cancer
Secondary Objectives
  To evaluate other response parameters for two different doses for Anti-EpCAM
  To evaluate the safety and tolerability of two different doses of Anti-EpCAM
  To determine the pharmacokinetics of two different doses of Anti-EpCAM
  To evaluate pharmacodynamics of two different doses of Anti-EpCAM
  To determine the pharmacokinetics of Anti-EpCAM in patients with metastatic breast cancer
  To evaluate the pharmacodynamics of Anti-EpCAM (NK cells)

Example 1.6

Investigational Plan

Study Endpoints; Primary Endpoint Clinical Benefit Rate (SD+PR+CR) at 24 Weeks
  The clinical benefit rate is defined as the proportion of patients with stable disease (SD)+partial response (PR)+complete response (CR), according to RECIST (see Example 1.18).
Study Endpoints; Secondary Endpoints
  Clinical benefit rate (SD+PR+CR) at 12 weeks
  Best overall tumor response rate (OTR)
  Duration of response/time to progression
  Incidence of adverse events and laboratory abnormalities
  Serum concentrations of Anti-EpCAM Number of peripheral natural killer (NK) cells Overall Study Design This is an open-label, multicenter, randomized, parallel group, phase II study investigating the efficacy and safety of two treatment doses of Anti-EpCAM in patients with low/moderate or high EpCAM expression over 24 weeks of therapy.

A total of 112 patients have been enrolled in the study. After the screening period, the patients meeting all illegibility criteria will be randomized within each EpCAM stratum to one of two treatment groups: a low dose group and a high dose group. Anti-EpCAM will be administered as a 60 minutes intravenous (i.v.) infusion weekly during the loading phase (Day 1, Day 8 and Day 15) and every second week thereafter, for a total of 24 weeks or until disease progression. Patients were stratified according to the level of their EpCAM expression. Here, there were two groups: those with low/moderate EpCAM expression, and those with high EpCAM expression. Table 2 shows an overview of this additional stratification.

TABLE 2

Stratified treatment groups and Anti-EpCAM doses

| Treatment Groups | EpCAM Expression | Anti-EpCAM Dosing |
|---|---|---|
| Group I | Moderate EpCAM expression on primary tumor | 2 mg/kg Anti-EpCAM i.v., every two weeks |
| Group II | Moderate EpCAM expression on primary tumor | 6 mg/kg Anti-EpCAM i.v., every two weeks |
| Group III | High EpCAM expression on primary tumor | 2 mg/kg Anti-EpCAM i.v., every two weeks |
| Group IV | High EpCAM expression on primary tumor | 6 mg/kg Anti-EpCAM i.v., every two weeks |

Patients will be monitored every 6 weeks until week 24 and every 8 weeks thereafter (during follow-up study), by a clinical assessment and laboratory tests. Further evaluations will be performed for the assessment of tumor response including thoracic CT scan or chest X-ray, abdominal CT scan or MRI, and bone scintigraphy if bone lesions were detected at screening.

The efficacy will be evaluated for each group, and the duration of response/time to progression will be compared to the expected values in this patient population. Tumor response as measured by RECIST (see Example 1.18) criteria will be assessed and used for statistical analysis.

The primary endpoint of the study is the clinical benefit rate (CR+PR+SD) at week 24 in each of the four groups. The clinical benefit rate (SD+PR+CR) at week 12, best overall tumor response rate (OTR), duration of response/time to progression will be evaluated as secondary endpoints. The safety and tolerability results will be compared between treatment groups at week 24.

If it becomes evident at any time during the study that one of the doses is preferable for efficacy or tolerability reasons, the study protocol will be amended accordingly.

Patients for whom SD, PR or CR is documented after 24 weeks of therapy and in whom no unacceptable toxicity (and no treatment interruption greater than 4 weeks) was reported, will be offered to participate in a follow-on study with continued Anti-EpCAM therapy. Parameters such as long-term tolerability, clinical progression and overall survival will be evaluated.

Example 1.7

Clinical Study Population

Inclusion Criteria
1. A patient will be eligible for study participation only if all of the following criteria apply:
2. Histologically confirmed metastatic breast cancer with positive EpCAM expression in the archived tissue samples determined by immunohistochemistry at screening
3. Presence of at least one lesion (i.e. metastasis) measurable in at least one dimension (according to RECIST (see Example 1.18))
4. Life expectancy≧12 months
5. ECOG performance status 0-1
6. Age≧18 years
7. Ability to understand and willingness to sign a written informed consent Exclusion Criteria A patient will not be eligible to participate in this study if any of the following criteria apply:
1. Any other treatment to be recommended/preferred at time of inclusion as per Investigator's assessment
2. History of CNS metastases
3. Indication for trastuzumab (Herceptin®) treatment as per Investigator's assessment
4. Immunotherapy, radiation, chemotherapy or any other anticancer therapy within 4 weeks prior to start of therapy except:
    Localized radiotherapy that started prior to visit 1 (target lesion cannot be within area of irradiation, and radiotherapy should not be expected to result in marrow suppression as defined in exclusion criterion 6)
    Hormonal treatment under which patient was progressive and which is terminated prior start of study treatment
5. Any investigational product within 4 weeks prior to the start of therapy
6. Abnormal organ or bone marrow function defined as follows:
    Hemoglobin concentration≦90 g/L of 9.0 g/dL
    Leukocytes<3×10$^9$/L (3000/mm$^3$)
    Platelet count<100×10$^9$/L (100,000/mm$^3$)
    AST(SGOT) or ALT(SGPT)>2× upper limit of normal (ULN) (>5×ULN if liver metastases present)
    Serum creatinine>1.5×ULN
    Serum lipase>1.5×ULN
    Serum amylase>1.5×ULN
7. History of malignancy other than breast cancer within 5 years prior to start of therapy, with the exception of basal cell carcinoma of the skin or carcinoma in situ of the cervix
8. Any other concurrent disease or medical condition that is deemed to interfere with the conduct of the study as judged by the investigator
9. Anticipated need, or regular use within 4 weeks prior to start of therapy, of immunosuppressive agents such as systemic corticosteroids
10. Known infection with human immunodeficiency virus (HIV) and/or infection with hepatitis B virus (HbsAg positive) or hepatitis C virus (anti-HCV positive)
11. Pregnant or nursing women, or women of childbearing potential not willing to use an effective form of contraception during participation in the study and at least 3 months thereafter 12. Known hypersensitivity to immunoglobulins or to any other component of the study drug formulation Example 1.8

Clinical Trial Material

Preparation

The investigational product Anti-EpCAM for clinical trial use is supplied as a solution in GMP quality, for example comprising 10 mg/mL Anti-EpCAM in isotonic phosphate buffer and is stored between +2 and +8° C.

The amount of Anti-EpCAM for the preparation of the final solution for infusion to a patient is calculated based on the patient's body weight and treatment group (see above Table 2).

Anti-EpCAM will be diluted in 500 mL 0.9% sodium chloride solution in a clean, sterile environment (laminar flow hood). To mix the final Anti-EpCAM solution for infusion, the bag should be inverted gently to avoid foaming. Both the concentrate and final solution for infusion are for single use only.

Treatment Assignment Procedure

Randomization will take place as close as possible to the start of Anti-EpCAM therapy. All eligibility criteria must be met at the time of randomization. A centralized randomization procedure will be provided by means of an ICRS (Interactive Computer Response System). The investigator has to login with an individual identification number and password onto a secured website where she/he has to provide basic patient data (patient number, data of screening, date of birth, EpCAM test results) in order to receive immediate response regarding treatment assignment. The randomization procedure does not stratify the treatment assignment by center but by EpCAM expression to ensure balanced distribution of high and low dose treatments in both EpCAM expression strata. As soon as the requested number of patients has been achieved in a treatment arm no further patients can be randomized to this respective arm.

The solution should be administered to the patient intravenously over 60 minutes, at a flow rate of 500 mL/h.

Example 1.9

Treatment

Treatment Schedule

Each patient will receive a total of 14 infusions of Anti-EpCAM over 24 weeks of therapy unless disease progression or treatment-limiting toxicity occurs. The Anti-EpCAM solution for infusion will be administered to the patient intravenously over 60 minutes, weekly during the loading phase and every second week during the maintenance phase. Prior to Visit 2 (Day 1), the patients will be randomized within each EpCAM expression stratum to one of the following treatment groups:

Groups I and III (low dose): loading phase of 2 mg Anti-EpCAM/kg body weight weekly (week 1, 2 and 3), followed by 11 maintenance doses of 2 mg Anti-EpCAM/kg body weight every second week Groups II and IV (high dose): loading phase of 6 mg Anti-EpCAM/kg body weight at weekly (week 1, 2 and 3), followed by 11 maintenance doses of 6 mg Anti-EpCAM/kg body weight every second week Randomization procedure will be centralized and stratified according to the EpCAM test result performed at screening. An interactive computer response system will be used to register EpCAM results and patient data. Upon registration of the data treatment assignment will be given for the patient. Calculation of the individual doses for a patient and preparation of the final solution for infusion will be performed at each center.

Patients for whom SD, PR or CR is documented after 24 weeks of therapy and in whom no unacceptable toxicity (and no treatment interruption greater than 4 weeks) was reported will be offered to participate in a follow-up study with continued Anti-EpCAM therapy.

Treatment Discontinuation for Adverse Events

The study medication may be interrupted or discontinued, or the dose may be reduced for patients in the high dose group, according to the severity and causality of the adverse event.

Should the investigator have compelling evidence that the adverse event is not caused by the study medication, the treatment should be continued. However, if the relationship of the adverse event to the study medication cannot be excluded, doses should be modified.

Patient Discontinuation Criteria

Treatment with the investigational product should be discontinued i.e. in the event of any of the following:

Disease progression, as defined by RECIST (see Example 1.18)

Withdrawal of patient's consent

Patient or investigator not compliant with the study protocol

Progression of a medical condition which in the opinion of the investigator should preclude further participation of the patient in the study Administration of non-permitted concomitant medication(s)

Investigator's decision that a change of therapy is in the patient's best interest Occurrence of a Grade 3 adverse event if
  the adverse event is seen as clinically significant by the investigator and
  does not resolve to ≦grade 2 prior to the next administration and
  is at least possibly related to the study medication.

Occurrence of a Grade 4 adverse event Dose interruption for more than 4 weeks

Occurrence of any adverse event which makes discontinuation desirable or necessary in the investigator's and/or the patient's opinion.

Prior to discontinuation of a patient, all examinations scheduled for the safety follow-up should also be performed to allow for the evaluation of the study endpoints (see Example 1.11).

Concomitant Medication

All concomitant medication should be recorded in the Case Report Form (CRF). The following medication and therapies are not allowed during the whole study period:

Any anti-tumor therapy other than the investigational product such as:
  Hormonal therapy
  Biological therapy
  Chemotherapy
  Radiation therapy (Exception: Localized radiotherapy that started prior to visit 1 (target lesion cannot be within area of irradiation, and radiotherapy should not be expected to result in marrow suppression as defined in exclusion criterion 6) Pre-menopausal patients treated with LHRH analogs (Hormone receptor+) could continue this treatment during the study provided that they progressed on LHRH analogs before study entry.

Chronic systemic high-dose corticosteroid therapy and other immunosuppressive therapies Any other investigational agent If required, supportive therapy should be administered as medically needed in accordance with standard practice and should be recorded in the CRF. Therapy with bisphosphonates is allowed for patients with bone metastasis at study entry.

Example 1.10

Assessments

Assessment of Eligibility/Efficacy

Informed Consent: Written informed consent must be obtained from each patient before any study specific procedure.

Inclusion/Exclusion: Assessment of the patient's eligibility should be performed as outlined above in Example 1.7—Clinical Study Population, including review of all laboratory measurements performed for screening.

Medical History/Current Medical Conditions: General and disease specific medical history including a history of past and current medical conditions; full history of the course of the patient's cancer, including tumor stage, other prognostic markers, information on prior anti-tumor therapies will be recorded at screening.

Concomitant Medication: All concomitant medications will be recorded throughout the study.

Hepatitis B and C Testing: Hepatitis B surface antigen (HBsAg) and Hepatitis C virus (HCV) antibody testing will be performed during the screening period to exclude an active infection with hepatitis B or C viruses.

Tumor Assessment: Tumor response will be defined according to the RECIST (see Example 1.18) criteria Bone Scintigraphy: Bone scintigraphy will be performed to assess the presence of bone metastasis at screening and at the final visit. Further scans to be performed if bone metastases are present at screening or if clinically indicated (e.g. occurrence of pain and elevation of alkaline phosphatase).

Thoracic Computerized-Tomography (CT) Scan or Chest X-ray: Thoracic CT or chest X-ray will be performed to document the presence of distant metastasis at screening and to evaluate response regularly during the treatment phase and at the final visit.

Abdominal CT Scan or MRI: Abdominal CT scan or MRI will be performed to assess the presence of distant metastasis at screening and to evaluate response regularly during treatment and at the final visit.

Assessment of Safety

Adverse Events: Adverse events (AEs) occurring during the treatment period and until 4 weeks after the last Anti-EpCAM infusion will be recorded. During the screening period, AEs related to study procedures should also be reported.

Serious Adverse Events: All serious adverse events (SAE) will be recorded during the entire study period, including the screening and the follow-up periods.

Physical Examination: A complete physical examination of all body systems including vitals signs will be performed at screening, at regular intervals during the treatment phase and at the final visit. A symptom directed physical examination will be performed throughout the study as appropriate, and all clinically relevant findings will be documented. On infusion days, physical examination should be performed before Anti-EpCAM infusion.

Vital Signs Monitoring: Body temperature (oral or tympanic), heart rate and blood pressure (systolic/diastolic) will be measured throughout the study as follows:
  prior to infusion
  every 15 minutes during infusion at visits 2 to 6
  every hour for up to 4 hours after end of the infusion at visits 2 to 6

ECOG Score: Assessment of the patient's performance status will be performed using the Eastern Cooperative Oncology Group (ECOG) score (see Table 6 in Example 1.19).

Electrocardiogram (ECG): Standard 12-lead ECG will be performed at screening, during the treatment phase and at the final visit. For each ECG, two printouts should be obtained, one for documentation at the site and one for evaluation by a central cardiologist.

Safety Laboratory Evaluations: Blood samples for safety laboratory evaluations will be taken at each study visit in the morning (before the infusion on infusion days) and the following analyses will be performed:
  Clinical chemistry: Aspartate transaminase (AST), alanine transaminase (ALT), γ-glutamyl transferase (GGT), alkaline phosphatase (AP), lactate dehydrogenase (LDH), total bilirubin, total protein, creatinine, urea, uric acid, glucose, calcium, sodium, potassium, chloride, phosphate, amylase, lipase, albumin, C-reactive protein (CRP).
  Hematology: Red blood cell count (RBC), hemoglobin, hematocrit, white blood cell count (WBC), differential blood count, and platelet count.
  Coagulation: Prothrombin time (PT, international normalized ratio [INR]), partial thromboplastin time (PTT) and fibrinogen.

Urinalysis: Presence of glucose, protein and blood in urine will be assessed by dipstick at each visit. On the days of Anti-EpCAM infusion, urinalysis should be performed before Anti-EpCAM infusion.

Pregnancy Test: A pregnancy test (β-human chorionic gonadotropine [β-HCG]) will be performed at screening and at the final visit in all women of childbearing potential.

Immunogenicity: Blood samples for the assessment of Anti-EpCAM immunogenicity will be taken at screening, at weeks 6 and 24 and the last two follow-up visits 17 and 18.

Pharmacodynamic Assessments

Natural Killer Cells: The number of natural killer (NK) cells will be measured by Fluorescence-Activated Cell Sorter (FACS).

Pharmacokinetic Assessments

Anti-EpCAM serum trough and peak levels will be measured at visits 2 to 6, during the treatment period every 6 to 8 weeks and the last three follow-up visits 16 to 18.

Analysis of EpCAM Expression

EpCAM expression will be assessed at screening, using the patients archived tumor material. EpCAM expression will be determined by immunohistochemistry in a central laboratory.

Only patient with EpCAM results, which are low/moderate or high can proceed with all screening procedures. Patients with negative EpCAM test result do not meet eligibility criteria and will be considered as screening failures.

If during the study a biopsy is performed (e.g. in case of new detected metastasis), tumor tissue should also be collected for analysis of EpCAM expression.

Example 1.11

Visit Schedule

The calculation of all study visits is based on baseline (Day 1), defined as the day of the first dose of Anti-EpCAM infusion.

Screening Period (Day −28 to Day −1)

Only those patients who have met all eligibility criteria will be assigned a patient number (see Example 1.8—Treatment Assignment Procedure).

All screening evaluations must be performed within 28 days of the first administration of the investigational product (Day 1). All results, including the EpCAM expression test should be available before a patient is declared eligible for study participation. Once the results from the laboratory evaluations are available and the patient meets all eligibility criteria, the investigator should proceed with the centralized randomization procedure (ICRS).

Treatment Period (Visits 2 to 15)

During the treatment period, the following procedures and assessments should be performed:

Vital Signs
Physical Examination
Safety Laboratory Evaluation
Urinalysis
Pharmacokinetics
NK cells
Immunogenicity
Concomitant Medication
Adverse Events and Serious Adverse Events
Chest X-ray/CT scan
Abdominal CT scan or MRI
Bone scintigraphy (if bone lesions detected at screening)
ECG (only at visit 6 and 15)

Safety Follow-Up Period and Final PK/PD Assessment (Visits 16-18)

Safety follow-up visits will be performed two and four weeks after the end of therapy. Visit 17 is the final safety follow-up visit.

The last study visit (Visit 18) is the Final PK/PD Assessment 12 weeks after the end of therapy.

End of Study Visit (Visit 17/Final)

The end of study visit should be performed at the last follow-up visit or at any time if the patient is prematurely discontinued from the study.

Complete Physical Examination
Vital Signs
12-lead ECG
ECOG
Safety laboratory evaluation
Urinalysis
Pregnancy test
Chest X-ray/CT scan
Bone scintigraphy
Abdominal CT scan or MRI
Pharmacokinetics
Immunogenicity
Concomitant Medication
Adverse Events and Serious Adverse Events Efficacy Follow-Up Period Patients will be followed for disease progression, other cancer treatment and survival every 3 months until 1 year after the end of participation in the study. Patients with stable disease, partial or complete response at week 24 will have the opportunity to enter into an open-label study, in which evaluation of disease progression and overall survival will be performed.

Example 1.12

Sample Storage

Serum samples for immunogenicity, NK cell count and PK will be stored at the study site frozen at −20° C.

Example 1.13

Safety Considerations

The investigator is responsible for the detection and documentation of events meeting the definition of an adverse event (AE) or a serious adverse event (SAE). This includes the evaluation of its seriousness, its severity, and the causal relationship to the investigational product and/or concomitant therapy.

Example 1.14

Adverse Events, Serious Adverse Events

Adverse Events

The following events, detected or diagnosed during or after administration of the investigational medicinal product, are adverse events:

Aggravation of a pre-existing illness or permanent disorder,
Increase in frequency or intensity of a pre-existing episodic event or condition,
Signs or symptoms detected or diagnosed after administration of the investigational medicinal product, even if they may have occurred or existed prior to study participation,
Marked hematological and other laboratory abnormalities and any events that led to an intervention, including withdrawal of test drug/investigational product treatment, dose reduction, or significant additional concomitant therapy.

Serious Adverse Event

A serious adverse event (experience) or reaction is any untoward medical occurrence or effect that at any dose:

Results in death, (1)
Is life-threatening, (2)
Requires hospitalization or prolongation of existing inpatient's hospitalization,
Results in persistent or significant disability or incapacity,
Is a congenital anomaly or birth defect.

Assessment of Severity: The severity (or intensity) of AEs is evaluated according to the grading scale provided in the Cancer Therapy Evaluation Program, Common Terminology Criteria for Adverse Events (CTCAE), version 3.0.

Example 1.15

Statistical Analysis

Statistical Methods and Determination of Study Variables

The aim of this study is to determine efficacy and safety of Anti-EpCAM. Therefore, a randomized phase II trial with two arms (low and high dose of Anti-EpCAM) is performed, in which each treatment arm shall be deemed as a standard single-stage phase II study. The decision whether a treatment proofs to show sufficient activity will be made for each treatment arm separately. Sample size estimation and primary statistical analysis are based on standard single-stage single-arm phase II designs.

Table 3 lists the measurements and/or data management processes that will be carried out to determine the primary and secondary study endpoints.

TABLE 3

Primary and secondary study objectives, derived variables and method of measurement.

| Objective | Endpoint | Measurement |
|---|---|---|
| *Primary* | | |
| To evaluate the clinical benefit of two different doses of Anti-EpCAM in patients with EpCAM positive, metastatic breast cancer | Clinical benefit rate at week 24 | Proportion of patients with SD, PR and CR at week 24 |
| *Secondary* | | |
| To evaluate other response parameters for two different doses for Anti-EpCAM | Clinical benefit rate at week 12 | Proportion of patients with SD, PR and CR at week 12 and 48 |
| | Best overall tumor response rate (OTR) | Proportion of patients achieving a PR/CR throughout study period |
| | Duration of response/time to progression | Median time to disease progression calculated using Kaplan-Meier-methodology |
| To evaluate the safety and tolerability of two different doses of Anti-EpCAM | Incidence of adverse events and laboratory abnormalities | Proportion of patients with events: number, intensity and relationship to study treatment (according to investigator) of laboratory abnormalities, clinical adverse events and serious adverse events |
| To determine the pharmacokinetics of two different doses of Anti-EpCAM | Serum concentrations of Anti-EpCAM | Serum concentrations of Anti-EpCAM at defined time-points |
| To evaluate pharmacodynamics of two different doses of Anti-EpCAM | Number of peripheral natural killer (NK) cells | % Increase/decrease in NK-cell counts over time |

Statistical Hypothesis: The following assumptions are made for the statistical hypothesis of the study:

The background clinical benefit rate for best supportive care is estimated to be $\leq 5\%$ ($p_0$). The future use of Anti-EpCAM in the described patient population (positive EpCAM expression) would be of considerable interest if the true clinical benefit rate ($\pi$) is $\geq 25\%$ ($p_1$).

For each treatment arm (low or high dose group within the low/moderate and the high EpCAM strata), the following hypotheses apply:

$H_{0ij}(\pi \leq p_{0ij})$: $p_{ij} \leq 5\%$ (background clinical benefit probability)

$H_{1ij}(\pi \geq p_{1ij})$: $p_{ij} \geq 25\%$ (clinical benefit probability of interest for Anti-EpCAM) with $p_i$ being the clinical benefit rate observed among the low/moderate EpCAM expression strata (j=1) and high EpCAM expression strata patients (j=2) treated with dose level i, with i=1 denoting the low dose level and i=2 indicating the high dose level.

Level of Significance, Multiple Comparisons and Multiplicity: A type I error of 5% and a type II error of 15% (power of 85%) are considered as adequate to determine the clinical benefit rates. No significance levels have to be adjusted neither due to multiple comparisons nor due to multiplicity (no confirmatory comparison between treatment arms will be performed).

Determination of Sample Size: The sample size estimation is based on Fleming's standard single-stage procedure but using the exact binomial distribution (A'Hern (2001). Statistics in Medicine 20: 859-66), and not the normal approximation to the binomial distribution (Fleming (1982). Biometrics 38: 143-51). This approach is preferred because normal approximations are incorrect for small sample sizes, and sample sizes and cut-off points based on exact distributions have the advantage that the calculated confidence intervals do not include $p_0$ if the cut-off point has been achieved. Therefore, sample size tables provided by A'Hern (A'Hern (2001). Statistics in Medicine 20: 859-66) are employed for this study.

According to these calculations, 24 patients evaluable for efficacy are required per arm for the study to have a 85% chance (i.e. power=85%) of demonstrating that the 95% one-sided confidence interval (i.e. type one error=5%) for the response rate excludes 5% ($p_0$) if the true overall response rate over 24 weeks is 25% ($p_1$).

Assuming that approximately 10% of the patients will not be evaluable with regard to efficacy (drop-outs), a total of at least 108 patients (54 in the low/moderate EpCAM strata with 27 of those treated with the low dose and 27 with the high dose and 54 in the high EpCAM expression strata with 27 of those treated with low dose and 27 with the high dose) should be randomized into the study.

Planned Analyses

Primary and secondary variables will be evaluated exploratively. All relevant data on patients (data from CRF, laboratory data) will be analyzed descriptively grouped by treatment arm and visits.

Individual patient data will be presented in listings (sorted by treatment arm and patient number). All data collected in the CRF and included in the database will be listed.

Demographic and Other Baseline Characteristics: Demographics and other baseline characteristics will be summarized in total and by treatment arm by means of summary statistics (number of patients, mean, standard deviation, minimum, median, maximum) for continuous variables and by absolute and relative frequencies for categorical variables.

Baseline characteristics are defined as all results of the examinations performed prior to the first Anti-EpCAM administration.

Planned Analyses for Primary Endpoint: The primary analysis will be based on the full analysis set, an analysis based on the per-protocol set will be performed as a sensitivity analysis. Primary endpoint of the study is the clinical benefit rate (patients with stable disease+CR+PR according to RECIST (see Example 1.18))

In a first step, the clinical benefit rate in each treatment arm will be evaluated separately. A 95% one-sided confidence interval will be calculated for the clinical benefit rate in each treatment arm. If the lower bound of the 95% one-sided confidence interval of the response rate is larger than $p_0=5\%$ in a treatment arm, the null hypothesis will be rejected for this treatment arm. The cut-off point in this study is 4, meaning that as soon as 4 patients with clinical benefit have been achieved in a treatment arm the null hypothesis for the respective treatment arm can be rejected Further analysis of the primary endpoint will include:

- If all treatment arms show sufficient activity, the treatment arms with the same dose level will be pooled and the dose levels will be compared allowing for unequal clinical benefit rates for patients with low/moderate and high EpCAM expression. The comparison of the two dose levels will be conducted by means of a logistic regression model with the two factors EpCAM expression and dose level, out of which the appropriate odds ratios for the two levels will be calculated
- If both dose levels show sufficient activity only in one of the patient populations (either with low/moderate EpCAM expression or with high EpCAM expression) these two dose levels will be compared descriptively.

Planned Analyses for Secondary Endpoints: Best overall tumor response rate at week 24 will be evaluated for each treatment arm and in the same way as described for the primary endpoint.

Adverse events will be summarized overall by treatment arm and by dose level, grouped by their primary system organ class, high level term, preferred term and severity.

No statistical comparison of the overall incidence of adverse events will be done between the treatment arms and dose levels.

Data will be summarized for all sample days overall, by treatment arm and by dose level. Absolute changes from baseline values for all post-baseline sample days will be summarized overall, by treatment arm and by dose level. Shift tables from baseline will be produced for urinalysis data overall, by treatment arm and by dose level.

Pharmacodynamic parameters will be analyzed descriptively by presenting summary statistics (mean, standard deviation, minimum, median and maximum) of raw data and changes from baseline for all study days overall, by treatment arm and by dose level.

Administrative Data Review

For the purpose of deciding on further strategies for subsequent studies with Anti-EpCAM, an administrative analysis of the best overall response rate will be performed,
- after 70 patients received at least one infusion and have passed Visit 9/week 12 or prematurely discontinued the study and
- data regarding the best overall response rate is considered to be reasonably clean Recruitment will not be stopped for this administrative analysis.

Example 1.16

Quality Control and Quality Assurance

Prior to enrolment of patients at a study site, specific regulatory documents must be available, such as independent ethics committee (IEC) approval and curricula vitae for investigator and study staff.

The study will be monitored by a qualified and appropriately trained person appointed by Study Sponsor.

Example 1.17

Legal and Ethical Requirements

This study will be conducted in accordance with the ICH Harmonized Tripartite Guideline Guidelines for Good Clinical Practice and all applicable laws and regulations, including the Declaration of Helsinki, June 1964, as modified by the 48th World Medical Association, Somerset West, Republic of South Africa, October 1996.

Patient Information and Informed Consent

The process for obtaining patient informed consent will be in accordance with all applicable regulatory requirements. Prior to including any patient in the clinical study, his/her free and expressed informed consent must be obtained in writing.

Example 1.18

RECIST Criteria

The following is a summary of the RECIST criteria used throughout the foregoing study.

Eligibility

Only patients with measurable disease at baseline should be included in protocols where objective tumor response is the primary endpoint.

Measurable disease—the presence of at least one measurable lesion. If the measurable disease is restricted to a solitary lesion, its neoplastic nature should be confirmed by cytology/histology.

Measurable lesions—lesions that can be accurately measured in at least one dimension with longest diameter$\geqq$20 mm using conventional techniques or $\geqq$10 mm with spiral CT scan.

Non-measurable lesions—all other lesions, including small lesions (longest diameter<20 mm with conventional techniques or <10 mm with spiral CT scan), i.e., bone lesions, leptomeningeal disease, ascites, pleural/pericardial effusion, inflammatory breast disease, lymphangitis cutis/pulmonis, cystic lesions, and also abdominal masses that are not confirmed and followed by imaging techniques.

All measurements should be taken and recorded in metric notation, using a ruler or calipers. All baseline evaluations should be performed as closely as possible to the beginning of treatment and never more than 4 weeks before the beginning of the treatment.

The same method of assessment and the same technique should be used to characterize each identified and reported lesion at baseline and during follow-up.

Clinical lesions will only be considered measurable when they are superficial (e.g., skin nodules and palpable lymph nodes). For the case of skin lesions, documentation by color photography, including a ruler to estimate the size of the lesion, is recommended.

Methods of Measurement

CT and MRI are the best currently available and reproducible methods to measure target lesions selected for response assessment. Conventional CT and MRI should be performed with cuts of 10 mm or less in slice thickness contiguously. Spiral CT should be performed using a 5 mm contiguous reconstruction algorithm. This applies to tumors of the chest, abdomen and pelvis. Head and neck tumors and those of extremities usually require specific protocols.

Lesions on chest X-ray are acceptable as measurable lesions when they are clearly defined and surrounded by aerated lung. However, CT is preferable.

When the primary endpoint of the study is objective response evaluation, ultrasound (US) should not be used to measure tumor lesions. It is, however, a possible alternative to clinical measurements of superficial palpable lymph nodes, subcutaneous lesions and thyroid nodules. US might also be useful to confirm the complete disappearance of superficial lesions usually assessed by clinical examination.

The utilization of endoscopy and laparoscopy for objective tumor evaluation has not yet been fully and widely validated. Their uses in this specific context require sophisticated equipment and a high level of expertise that may only be available in some centers. Therefore, the utilization of such techniques for objective tumor response should be restricted to validation purposes in specialized centers. However, such techniques can be useful in confirming complete pathological response when biopsies are obtained.

Tumor markers alone cannot be used to assess response. If markers are initially above the upper normal limit, they must normalize for a patient to be considered in complete clinical response when all lesions have disappeared.

Cytology and histology can be used to differentiate between PR and CR in rare cases (e.g., after treatment to differentiate between residual benign lesions and residual malignant lesions in tumor types such as germ cell tumors).

Baseline Documentation of "Target" and "Non-Target" Lesions

All measurable lesions up to a maximum of five lesions per organ and 10 lesions in total, representative of all involved organs should be identified as target lesions and recorded and measured at baseline.

Target lesions should be selected on the basis of their size (lesions with the longest diameter) and their suitability for accurate repeated measurements (either by imaging techniques or clinically).

A sum of the longest diameter (LD) for all target lesions will be calculated and reported as the baseline sum LD. The baseline sum LD will be used as reference by which to characterize the objective tumor.

All other lesions (or sites of disease) should be identified as non-target lesions and should also be recorded at baseline. Measurements of these lesions are not required, but the presence or absence of each should be noted throughout follow-up.

| Response Criteria | |
|---|---|
| Evaluation of target lesions | |
| * Complete Response (CR): | Disappearance of all target lesions |
| * Partial Response (PR): | At least a 30% decrease in the sum of the LD of target lesions, taking as reference the baseline sum LD |
| * Progressive Disease (PD): | At least a 20% increase in the sum of the LD of target lesions, taking as reference the smallest sum LD recorded since the treatment started or the appearance of one or more new lesions |
| * Stable Disease (SD): | Neither sufficient shrinkage to qualify for PR nor sufficient increase to qualify for PD, taking as reference the smallest sumLD since the treatment started |
| Evaluation of non-target lesions | |
| * Complete Response (CR): | Disappearance of all non-target lesions and normalization of tumor marker level |
| * Incomplete Response/ Stable Disease (SD): | Persistence of one or more non-target lesion(s) or/and maintenance of tumor marker level above the normal limits |
| * Progressive Disease (PD): | Appearance of one or more new lesions and/ or unequivocal progression of existing non-target lesions (1) |

(1) Although a clear progression of "non target" lesions only is exceptional, in such circumstances, the opinion of the treating physician should prevail and the progression status should be confirmed later on by the review panel (or study chair).

Evaluation of Best Overall Response

The best overall response is the best response recorded from the start of the treatment until disease progression/recurrence (taking as reference for PD the smallest measurements recorded since the treatment started). In general, the patient's best response assignment will depend on the achievement of both measurement and confirmation criteria

| Target lesions | Non-Target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or No | PD |
| Any | PD | Yes or No | PD |
| Any | Any | Yes | PD |

Patients with a global deterioration of health status requiring discontinuation of treatment without objective evidence of disease progression at that time should be classified as having "symptomatic deterioration". Every effort should be made to document the objective progression even after discontinuation of treatment.

In some circumstances it may be difficult to distinguish residual disease from normal tissue. When the evaluation of complete response depends on this determination, it is recommended that the residual lesion be investigated (fine needle aspirate/biopsy) to confirm the complete response status.

Confirmation

The main goal of confirmation of objective response is to avoid overestimating the response rate observed. In cases where confirmation of response is not feasible, it should be made clear when reporting the outcome of such studies that the responses are not confirmed.

To be assigned a status of PR or CR, changes in tumor measurements must be confirmed by repeat assessments that should be performed no less than 4 weeks after the criteria for response are first met. Longer intervals as determined by the study protocol may also be appropriate.

In the case of SD, follow-up measurements must have met the SD criteria at least once after study entry at a minimum interval (in general, not less than 6-8 weeks) that is defined in the study protocol.

Duration of Overall Response

The duration of overall response is measured from the time measurement criteria are met for CR or PR (whichever status is recorded first) until the first date that recurrence or PD is objectively documented, taking as reference for PD the smallest measurements recorded since the treatment started.

Duration of Stable Disease

SD is measured from the start of the treatment until the criteria for disease progression are met, taking as reference the smallest measurements recorded since the treatment started. The clinical relevance of the duration of SD varies for different tumor types and grades. Therefore, it is highly recommended that the protocol specify the minimal time interval required between two measurements for determination of SD. This time interval should take into account the expected clinical benefit that such a status may bring to the population under study.

Response Review

For trials where the response rate is the primary endpoint it is strongly recommended that all responses be reviewed by an expert(s) independent of the study at the study's completion. Simultaneous review of the patients' files and radiological images is the best approach.

Reporting of Results

All patients included in the study must be assessed for response to treatment, even if there are major protocol treatment deviations or if they are ineligible. Each patient will be assigned one of the following categories: 1) complete response, 2) partial response, 3) stable disease, 4) progressive disease, 5) early death from malignant disease, 6) early death from toxicity, 7) early death because of other cause, or 9) unknown (not assessable, insufficient data). All of the patients who met the eligibility criteria should be included in the main analysis of the response rate. Patients in response categories 4-9 should be considered as failing to respond to treatment (disease progression). Thus, an incorrect treatment schedule or drug administration does not result in exclusion from the analysis of the response rate. Precise definitions for categories 4-9 will be protocol specific.

All conclusions should be based on all eligible patients.

Subanalyses may then be performed on the basis of a subset of patients, excluding those for whom major protocol deviations have been identified (e.g., early death due to other reasons, early discontinuation of treatment, major protocol violations, etc.). However, these subanalyses may not serve as the basis for drawing conclusions concerning treatment efficacy, and the reasons for excluding patients from the analysis should be clearly reported.

The 95% confidence intervals should be provided.

Example 1.19

Overview of ECOG Performance Status

The ECOG performance status scale is disclosed in Oken, M. M. et al. (1982) Am J Clin Oncol 5:649-655.

Example 2

Administrative Data Review for Phase II Clinical study of Anti-EpCAM

Example 2.1

Summary and Introduction to Study

The clinical study was performed as described above in Example 1. The results of this study follow now in Example 2.

Methodology:

A randomized, open-label, multicenter, parallel group, phase II study. The study was designed to evaluate the efficacy and safety of Anti-EpCAM over 24 weeks of therapy at two different doses with positive EpCAM testing. The central randomization process was stratified according to the EpCAM test results performed at screening. Upon registration in one of the EpCAM strata, patients were randomly assigned to either the low dose treatment group or the high dose treatment group.

Number of patients randomized and treated: 112 (28 patients are still ongoing)

Number of patients analyzed: 73 treated patients (37 Anti-EpCAM high dose, 36 Anti-EpCAM low dose)

Data Analyzed for the Foregoing Analysis:

All data leading to these results were monitored according to GCP-requirements but without data cleaning complete. The CRFs of all patients completing all visits until week 12 and having all required tumor assessments at week 6 and 12 (n=23) were subject of a medical review with the emphasis to detect major protocol deviations and to clean the safety data.

For these 23 patients the radiologic data were centrally reviewed for this analysis.

Definition of Populations for Analysis:

Safety Analysis Set (SAF): All patients who received at least one dose of the assigned study medication.

Full Analysis Set (FAS): Patients from the Safety Analysis Set who had EpCAM positive (low/moderate or high expression) tumors and at least one tumor assessment after start of therapy in case of early withdrawal due to other reasons than clinical disease progression.

The analysis of safety data was based on the SAF.

The analysis of baseline data and efficacy endpoints was based on the full analysis sets.

Analyzed Endpoints (cf. Example 1.1, Above):

Best Overall Tumor Response (OTR) rate at Week 12 (patients with complete remission [CR] or partial remission [PR] according to RECIST)

Clinical Benefit Rate (CBR) at Week 12 (patients with stable disease or complete remission [CR] or partial remission [PR] according to RECIST)

Clinical Benefit Rate (CBR) at Week 24 (patients with stable disease or complete remission [CR] or partial remission [PR] according to RECIST)

Time to Progression (TTP) as time from randomization and alternatively time from start of treatment.

Subgroups Analyzed:

High, moderate and low EPCAM expressors were identified according to Gastl et al. (2000). Lancet 356, 1981-2.

The following subgroups were analyzed:

EpCAM low/moderate expressors treated with low dose Anti-EpCAM ("low dose Anti-EpCAM/low EpCAM")

EpCAM low/moderate expressors treated with high dose Anti-EpCAM ("high dose Anti-EpCAM/low EpCAM")

EpCAM high expressors treated with low dose Anti-EpCAM ("low dose Anti-EpCAM/high EpCAM")

EpCAM high expressors treated with high dose Anti-EpCAM ("high dose Anti-EpCAM/high EpCAM")

EpCAM low/moderate expressors treated with low or high dose Anti-EpCAM ("low EpCAM")

EpCAM high expressors treated with low or high dose Anti-EpCAM ("high EpCAM")

Low dose Anti-EpCAM in EpCAM low/moderate or EpCAM high expressors ("low dose Anti-EpCAM")

High dose Anti-EpCAM in EpCAM low/moderate or EpCAM high expressors ("high dose Anti-EpCAM").

Analyses Performed:

Response (CBR or OTR) endpoints as defined above were analyzed as follows:
  CBR/OTR rate for each subgroup (see above) and all patients.
  Fisher's exact test for CBR/OTR rate for the following comparisons:
  each subgroup (see above) vs. all other patients combined
  "low dose Anti-EpCAM/low EpCAM" vs. "low dose Anti-EpCAM/high EpCAM"
  "low dose Anti-EpCAM/low EpCAM" vs. "high dose Anti-EpCAM/low EpCAM"
  "high dose Anti-EpCAM/high EpCAM" vs. "low dose Anti-EpCAM/high EpCAM"
  "high dose Anti-EpCAM/high EpCAM" vs. "high dose Anti-EpCAM/low EpCAM".

Time to clinical disease progression was defined as duration between the date of the first Anti-EpCAM infusion (alternatively in a sensitivity analysis: date of randomization) and the date of clinical disease progression, i.e. the first incidence of progressive disease, respectively. If no clinical disease progression was observed, the respective time span was censored with the date of study termination. In case of a missing date for study termination, the date of the last visit performed was used instead.

Time-To-Progression (TTP) endpoints were analyzed as follows:
  Median TTP (if estimable) for each subgroup and all patients.
  Log-Rank test for TTP for the following comparisons:
    each subgroup vs. all other patients combined
    "low dose Anti-EpCAM/low EpCAM" vs. "low dose Anti-EpCAM/high EpCAM"
    "low dose Anti-EpCAM/low EpCAM" vs. "high dose Anti-EpCAM/low EpCAM"
    "high dose Anti-EpCAM/high EpCAM" vs. "low dose Anti-EpCAM/high EpCAM"
    "high dose Anti-EpCAM/high EpCAM" vs. "high dose Anti-EpCAM/low EpCAM".

Example 2.2

Results—Study Patients

Datasets Analyzed

Populations for analysis are tabulated in Table 4.

The full analysis set (FAS) (n=67) represents the analysis population for response and time to progression assessment. EpCAM status was equally distributed in the two Anti-EpCAM dose groups, with about 38% of low-EpCAM expressors and 57% of high EpCAM expressors in each treatment group.

TABLE 4

Populations for Analysis[1]

| Patients | | Total (N = 73) | | Low Dose Anti-EpCAM (N = 36) | | High Dose Anti-EpCAM (N = 37) | |
|---|---|---|---|---|---|---|---|
| | | n | % | n | % | n | % |
| Total | Safety Analysis Set (SAF) | 73 | 100.0 | 36 | 100.0 | 37 | 100.0 |
| | Full Analysis Set (FAS)[2] | 67 | 91.8 | 32 | 88.9 | 35 | 94.6 |
| EpCAM Negative | Total | 3 | 4.1 | 1 | 2.8 | 2 | 5.4 |
| | Safety Analysis Set (SAF) | 3 | 100.0 | 1 | 100.0 | 2 | 100.0 |
| | Full Analysis Set (FAS)[2] | 0 | 0.0 | 0 | 0.0 | 0 | 0.0 |
| EpCAM Low/Intermediate | Total | 28 | 38.4 | 14 | 38.9 | 14 | 37.8 |
| | Safety Analysis Set (SAF) | 28 | 100.0 | 14 | 100.0 | 14 | 100.0 |
| | Full Analysis Set (FAS)[2] | 27 | 96.4 | 13 | 92.9 | 14 | 100.0 |
| EpCAM High | Total | 42 | 57.5 | 21 | 58.3 | 21 | 56.8 |
| | Safety Analysis Set (SAF) | 42 | 100.0 | 21 | 100.0 | 21 | 100.0 |
| | Full Analysis Set (FAS)[2] | 40 | 95.2 | 19 | 90.5 | 21 | 100.0 |

[1]Number of patients included in the administrative data review (%)
[2]Full Analysis Set (FAS): Patients from the Safety Analysis Set who had EpCAM positive (low/moderate or high expression) tumors and at least one tumor assessment after start of therapy in case of early withdrawal due to other reasons than clinical disease progression.

Example 2.3

Results—Efficacy Analysis for Overall Tumor Response (OTR) and Clinical Benefit Rate (CBR)

According to the study protocol the primary endpoint of the study is the clinical benefit rate at week 24.

"Best Overall Tumor Response (OTR)"

The results for the "Best Overall Tumor Response (OTR) rate at Week 12", the "Clinical Benefit Rate (CBR) at Week 12" and the "Clinical Benefit Rate (CBR) at Week 24" in the FAS for EpCAM high and low expressors and overall are presented in the following Table 5 and Table 6.

Response in terms of PR or CR according to RECIST criteria could not be confirmed in any patient of the FAS in the central radiologic assessment.

"Clinical Benefit Rate (CBR)" at W12

Overall, 16 out of 67 patients (24%) of the FAS showed disease stabilization (SD) at week 12. No significant difference between treatment groups was seen with regard to the clinical benefit rate at week 12, which was 21.9% in the low dose group and 25.7% in the high dose group.

The CBR was higher in the high EpCAM groups than in the low EpCAM groups, however this difference was statistically not significant.

The Clinical Benefit Rate only comprised patients with stable disease as remissions according to RECIST could not be detected (see above).

TABLE 5

Clinical Benefit Rate (CBR) at Week 12 (patients with stable disease or complete remission [CR] or partial remission [PR] according to RECIST) - Full Analysis Set

|  | Low Dose Anti-EpCAM[1] | | High Dose Anti-EpCAM[1] | | |
| --- | --- | --- | --- | --- | --- |
|  | n | % | n | % | P-Value[2] |
| Low EpCAM (N[3] = 13/14) | 2 | 15.4 | 2 | 14.3 | 1.0 |
| High EpCAM (N[3] = 19/21) | 5 | 26.3 | 7 | 33.3 | 0.7365 |
| Overall (N[3] = 32/35) | 7 | 21.9 | 9 | 25.7 | 0.7797 |

[1]Number of patients with clinical benefit among patients for which clinical benefit could be assessed according to RECIST
[2]Two-sided Fisher's Exact Test
[3]N in low dose group/high dose group "Clinical Benefit Rate (CBR)" at W24

A higher clinical benefit rate was seen at week 24 in the high dose group (14.3%) as compared to the low dose group (6.3%). In the high dose group the CBR is identical (14.3%) for the low and high EpCAM subgroups. In the low dose group the CBR is similar for the high and low EpCAM expressors (5.3 vs. 7.7%).

The CBR is only based on patients with stable disease as no PR or CR were detected.

TABLE 6

Clinical Benefit Rate (CBR) at Week 24 (patients with stable disease or complete remission [CR] or partial remission [PR] according to RECIST)

|  | Low Dose Anti-EpCAM[1] | | High Dose Anti-EpCAM[1] | | |
| --- | --- | --- | --- | --- | --- |
|  | n | % | n | % | P-Value[2] |
| Low EpCAM (N[3] = 13/14) | 1 | 7.7 | 2 | 14.3 | 1.0 |
| High EpCAM (N[3] = 19/21) | 1 | 5.3 | 3 | 14.3 | 0.6039 |
| Overall (N[3] = 32/35) | 2 | 6.3 | 5 | 14.3 | 0.4266 |

[1]Number of patients with clinical benefit among patients for which clinical benefit could be assessed according to RECIST
[2]Two-sided Fisher's Exact Test
[3]N in low dose group/high dose group Efficacy Analysis: Time to Progression Time to clinical disease progression was defined as duration between the date of the first Anti-EpCAM infusion (alternatively in the sensitivity analysis: date of randomization) and the date of clinical disease progression, i.e. the first incidence of progressive disease according to RECIST. If no clinical disease progression was observed, the time span to the date of study termination was taken. In case the date of study termination was not available, the date of the last visit performed was taken instead.

Median time to progression in the FAS for the low and high dose group and the EpCAM subgroups is presented in Table 7 (time from start of treatment to clinical disease progression) and Table 8 (time from randomization to clinical disease progression).

Overall Anti-EpCAM high dose showed a clear prolongation of the median time to progression (calculated as time from first infusion) from 43 to 78 days when compared to the Anti-EpCAM low dose treatment (as shown in FIG. 2). This difference was statistically significant when testing the "survival" curves (p=0.0348; log rank test) (as shown in FIG. 3). Similar, a difference in median time to progression (calculated as time from first infusion) was observed when comparing patients with low versus high EpCAM expression (42 to 80 days, respectively; p=0.0431; log rank test). The highest median time to progression (calculated as time from first infusion) was observed in patients with high EpCAM expression treated with high dose of Anti-EpCAM (90 days; p=0.0238; log rank test—compared to all other patients) (as shown in FIG. 5).

TABLE 7

Median Time to Progression (time from start of infusion to clinical disease progression [days]) - Full Analysis Set

|  | Low Dose Anti-EpCAM[1] | High Dose Anti-EpCAM[1] | P-Value[2] |
| --- | --- | --- | --- |
| Low EpCAM (N[3] = 13/14) | 41 days | 47 days | 0.1451 |
| High EpCAM (N[3] = 19/21) | 49 days | 90 days | 0.1262 |
| Overall (N[3] = 32/35) | 43 days | 78 days | 0.0348 |

[1]Median time to progression in days
[2]Log Rank Test on differences between treatment groups
[3]N in low dose group/high dose group The data of Table 7 are graphically represented in FIG. 4.

For the time to progression calculated from the day of randomization comparable results were found. Again overall Anti-EpCAM high dose showed a clear prolongation of the median time to progression (calculated as time from randomization) from 46 to 79 days in comparison to the Anti-EpCAM low dose treatment. This difference was statistically significant when testing the "survival" curves (p=0.0441; log rank test). The treatment difference was also more pronounced in the high EpCAM group with median times to progression of 63 and 91 days for the low dose and high dose high EpCAM groups, respectively, and 43 and 53 days in the low dose and high dose low EpCAM group, respectively.

TABLE 8

Median Time to Progression (time from randomization to clinical disease progression [days]) - Full Analysis Set

|  | Low Dose Anti-EpCAM[1] | High Dose Anti-EpCAM[1] | P-Value[2] |
| --- | --- | --- | --- |
| Low EpCAM (N[3] = 13/14) | 43 days | 53 days | 0.2353 |
| High EpCAM (N[3] = 19/21) | 63 days | 91 days | 0.1350 |
| Overall (N[3] = 32/35) | 46 days | 79 days | 0.0441 |

Efficacy Conclusions

Based on the study protocol
The best overall response (OTR)
The clinical benefit rate (CBR); and
The time to progression (TTP)

were analyzed comparing the high dose Anti-EpCAM group and the low dose Anti-EpCAM group in the overall population and the low- and high-EpCAM subgroups.

The clinical benefit rates at weeks 12 and 24 (W12 and W24, respectively) could be established comprising all patients showing stable disease at the respective time points.

At W12 the CBR was slightly higher in the high dose Anti-EpCAM group than in the low dose group (25.7% vs. 21.9%), also showing higher rates in both dosage groups for the high EpCAM subgroups.

At W24 the CBR was higher in the high dose Anti-EpCAM group (14.3% vs. 6.3% in the low dose Anti-EpCAM group). No marked differences between the EpCAM subgroups could be detected.

The median time to progression in the overall sample showed a clear prolongation for the Anti-EpCAM high dose compared to the Anti-EpCAM low dose (43 to 78 days), the difference being statistically significant when testing the survival curves (p=0.0348, log rank test). The median time to progression (calculated as time from first infusion) was observed in patients with high EpCAM expression treated with high dose of Anti-EpCAM (90 days; p=0.0238; log rank test—compared to all other patients).

OVERALL CONCLUSIONS

The data available showed long-term disease stabilization (>week 24) in at least 7 patients with some patients still ongoing.

As is clearly visible in FIGS. 2-5, the time to progression evaluation showed a pronounced prolongation of "survival time" in favor of the high dose Anti-EpCAM population reaching statistical significance. Specifically, as shown in FIG. 5, the patient with high EpCAM expression receiving high doses of Anti-EpCAM significantly prolonged progression-free survival (90 days versus 41-49 days in the other groups).

Example 3

Final Study Report for Phase II Clinical study of Anti-EpCAM

Example 3.1

Summary and Introduction to Study

The clinical study was performed as described above in Example 1. The results of this study follow now in Example 3.
Methodology:
  A randomized, open-label, multicenter, parallel group, phase II study. The study was designed to evaluate the efficacy and safety of Anti-EpCAM over 24 weeks of therapy at two different doses with positive EpCAM testing. The central randomization process was stratified according to the EpCAM test results performed at screening. Upon registration in one of the EpCAM strata, patients were randomly assigned to either the low dose treatment group or the high dose treatment group.
  Number of patients randomized and treated: 112
  Number of patients analyzed: 112 treated patients (56 Anti-EpCAM high dose, 56 Anti-EpCAM low dose), thereof 109 patients tested EpCAM+.
Data Analyzed for the Foregoing Analysis:
  All data leading to these results were monitored and cleaned according to GCP-requirements and the database was locked before the final analysis was performed.
Definition of Populations for Analysis:
  Safety Analysis Set (SAF): All patients who received at least one dose of the assigned study medication.
  Full Analysis Set (FAS): Patients from the Safety Analysis Set who had EpCAM positive (low/moderate or high expression) tumors and at least one tumor assessment after start of therapy in case of early withdrawal due to other reasons than clinical disease progression.
  The analysis of safety data was based on the SAF.
  The analysis of baseline data and efficacy endpoints was based on the full analysis set.
Analyzed Endpoints: (Cf. Example 1.1, Above):
  Clinical Benefit Rate (CBR) at Week 24 (patients with stable disease [SD] or complete remission [CR] or partial remission [PR] according to RECIST)
  Best Overall Tumor Response (OTR) rate at Week 12 (patients with complete remission [CR] or partial remission [PR] according to RECIST)
  Clinical Benefit Rate (CBR) at Week 12 (patients with stable disease [SD] or complete remission [CR] or partial remission [PR] according to RECIST)
  Time to Progression (TTP) as time from randomization and alternatively time from start of treatment.
Subgroups Analyzed:
  High and low/moderate EPCAM expressors were identified according to Gastl et al. (2000). Lancet 356, 1981-2.
  The following subgroups were analyzed:
  EpCAM low/moderate expressors treated with low dose Anti-EpCAM ("low dose Anti-EpCAM/low EpCAM")
  EpCAM low/moderate expressors treated with high dose Anti-EpCAM ("high dose Anti-EpCAM/low EpCAM")
  EpCAM high expressors treated with low dose Anti-EpCAM ("low dose Anti-EpCAM/high EpCAM")
  EpCAM high expressors treated with high dose Anti-EpCAM ("high dose Anti-EpCAM/high EpCAM")
  EpCAM low/moderate expressors treated with low or high dose Anti-EpCAM ("low EpCAM")
  EpCAM high expressors treated with low or high dose Anti-EpCAM ("high EpCAM")
  Low dose Anti-EpCAM in EpCAM low/moderate or EpCAM high expressors ("low dose Anti-EpCAM")
  High dose Anti-EpCAM in EpCAM low/moderate or EpCAM high expressors ("high dose Anti-EpCAM").
Analyses Performed:
  Response (CBR or OTR) endpoints as defined above were analyzed as follows:
  CBR/OTR rate for each subgroup (see above) and all patients.
  Time to clinical disease progression was defined as duration between the date of the first Anti-EpCAM infusion (alternatively in a sensitivity analysis: date of randomization) and the date of clinical disease progression, i.e. the first incidence of progressive disease, respectively. If no clinical disease progression was observed, the respective time span was censored with the date of study termination. In case of a missing date for study termination, the date of the last visit performed was used instead.
Time-to-Progression (TTP) Endpoints were Analyzed as Follows:
  Median TTP (if estimable) for each subgroup and all patients.
  Log-Rank test for TTP on differences between the treatment groups for the following comparisons:
    each subgroup vs. all other patients combined
    "low dose Anti-EpCAM/low/moderate EpCAM" vs. "low dose Anti-EpCAM/high EpCAM"
    "low dose Anti-EpCAM/low/moderate EpCAM" vs. "high dose Anti-EpCAM/low/moderate EpCAM"
    "high dose Anti-EpCAM/high EpCAM" vs. "low dose Anti-EpCAM/high EpCAM"
    "high dose Anti-EpCAM/high EpCAM" vs. "high dose Anti-EpCAM/low/moderate EpCAM".
    "low dose Anti-EpCAM/low/moderate EpCAM" vs. "high dose Anti-EpCAM/high EpCAM"
    "low dose Anti-EpCAM" vs. "high dose Anti-EpCAM"
    "high EpCAM" vs. "low/moderate EpCAM"

Example 3.2

Results—Study Patients

Datasets Analyzed

Populations for analysis are tabulated in Table 9.

The full analysis set (FAS) (n=109) represents the analysis population for response and time to progression assessment.

TABLE 9

| | Populations for Analysis1 | | | | | | | |
|---|---|---|---|---|---|---|---|---|
| | Low Dose MT201 (N = 55) | | | | High Dose MT201 (N = 54) | | | |
| | Low/Moderate EpCAM (N = 19) | | High EpCAM (N = 36) | | Low/Moderate EpCAM (N = 16) | | High EpCAM (N = 38) | |
| | n | % | n | % | n | % | n | % |
| Race[2] Caucasian | 19 | 100 | 36 | 100 | 16 | 100 | 38 | 100 |
| Age [years][1] | n = 19 | | n = 36 | | n = 16 | | n = 38 | |
| | 60.3 ± 9.8 | | 59.2 ± 9.6 | | 57.8 ± 11.5 | | 59.1 ± 11.5 | |
| | (42.0-79.0, 61.0) | | (42.0-75.0, 61.5) | | (40.0-80.0, 54.5) | | (38.0-81.0, 60.5) | |
| Height [cm][1] | n = 19 | | n = 36 | | n = 16 | | n = 38 | |
| | 160.8 ± 7.9 | | 161.8 ± 6.6 | | 160.4 ± 6.9 | | 162.4 ± 7.5 | |
| | (149.0-177.0, 161.0) | | (150.0-175.0, 162.5) | | (150.0-170.0, 161.5) | | (145.0-176.0, 162.5) | |
| Weight [kg][1] | n = 19 | | n = 36 | | n = 16 | | n = 38 | |
| | 67.1 ± 6.5 | | 70.1 ± 13.2 | | 68.1 ± 7.9 | | 69.0 ± 15.3 | |
| | (57.0-75.0, 69.0) | | (50.0-108.0, 68.5) | | (53.5-84.0, 66.5) | | (42.7-115.0, 65.0) | |
| BMI [kg/m$^2$][1] | n = 19 | | n = 36 | | n = 16 | | n = 38 | |
| | 26.1 ± 3.1 | | 26.8 ± 4.8 | | 26.7 ± 4.1 | | 26.2 ± 5.9 | |
| | (20.4-31.6, 26.2) | | (19.3-39.7, 26.7) | | (18.7-33.8, 27.2) | | (17.1-49.1, 25.4) | |

[1]Number of patients, mean ± standard deviation (minimum-maximum, median)
[2]Number of patients, %

Example 3.3

Results—Efficacy Analysis for Overall Tumor Response (OTR) and Clinical Benefit Rate (CBR)

According to the study protocol the primary endpoint of the study is the clinical benefit rate at week 24.

"Best Overall Tumor Response (OTR)"

The results for the "Best Overall Tumor Response (OTR) rate at Week 12", the "Clinical Benefit Rate (CBR) at Week 12" and the "Clinical Benefit Rate (CBR) at Week 24" in the FAS for EpCAM high and low expressors and overall are presented in the following Table 10 and Table 11.

Two responses (in terms of PR or CR according to RECIST criteria) were diagnosed by local radiologic assessments but could not be confirmed in any patient of the FAS in the central radiologic assessment.

"Clinical Benefit Rate (CBR)" at W24

A trend towards higher clinical benefit rate (CBR), albeit not significant, was seen at week 24 in the high dose group (7.9%) as compared to the low dose group (4.5%). Similarly, the CBR for the high EpCAM expressors shows a trend towards higher CBR rates as compared to low/moderate EpCAM expressors (7.3% vs. 3.7%).

The CBR is only based on patients with stable disease as no PR or CR were detected.

TABLE 11

Clinical Benefit Rate (CBR) at Week 24
(patients with stable disease or complete remission [CR] or partial remission [PR] according to RECIST)

| | Low Dose MT201 (N = 44) | | | | High Dose MT201 (N = 38) | | | |
|---|---|---|---|---|---|---|---|---|
| | Low/Moderate EpCAM (N = 15) | | High EpCAM (N = 29) | | Low/Moderate EpCAM (N = 12) | | High EpCAM (N = 26) | |
| | n[1] | %[1] | n[1] | %[1] | n[1] | %[1] | n[1] | %[1] |
| Clinical Benefit[2] (CR, PR and SD) | 0 | 0.0 | 2 | 6.9 | 1 | 8.3 | 2 | 7.7 |
| No Clinical Benefit[2] (PD and Not Available) | 15 | 100.0 | 26 | 89.7 | 11 | 91.7 | 24 | 92.3 |
| Not Evaluable[2,3] | 0 | 0.0 | 1 | 3.4 | 0 | 0.0 | 0 | 0.0 |
| Lower 95% Confidence Limit for CBR | | 0.0% | | 1.2% | | 0.4% | | 1.4% |

[1]Number of patients (%)
[2]According to 'final' assessment
[3]patients still in the study with respective response assessment classified as 'not assessable' in the central/IRAB assessment "Clinical Benefit Rate (CBR)" at W12

Overall, 17 out of 109 patients (16%) of the FAS showed disease stabilization (SD) at week 12. A trend towards higher clinical benefit rate (CBR), albeit not significant, was seen at week 12 in the high dose group (16.7%) as compared to the low dose group (14.5%). Similarly, the CBR for the high EpCAM expressors shows a trend towards higher CBR rates as compared to low/moderate EpCAM expressors (18.9% vs. 8.6%).

TABLE 10

Clinical Benefit Rate (CBR) at Week 12 (patients with stable disease or complete remission [CR] or partial remission [PR] according to RECIST) - Full Analysis Set

|  | Low Dose MT201 (N = 55) | | | | High Dose MT201 (N = 54) | | | |
| --- | --- | --- | --- | --- | --- | --- | --- | --- |
|  | Low/Moderate EpCAM (N = 19) | | High EpCAM (N = 36) | | Low/Moderate EpCAM (N = 16) | | High EpCAM (N = 38) | |
|  | n[1] | %[1] | n[1] | %[1] | n[1] | %[1] | n[1] | %[1] |
| Clinical Benefit[2] (CR, PR and SD) | 1 | 5.3 | 7 | 19.4 | 2 | 12.5 | 7 | 18.4 |
| No Clinical Benefit[2] (PD and Not Available) | 18 | 94.7 | 28 | 77.8 | 14 | 87.5 | 28 | 73.7 |
| Not Evaluable[2,3] | 0 | 0.0 | 1 | 2.8 | 0 | 0.0 | 3 | 7.9 |

[1]Number of patients (%)
[2]According to 'final' assessment
[3]patients still in the study with respective response assessment classified as 'not assessable' in the central/IRAB assessment Efficacy Analysis: Time to Progression Time to clinical disease progression was defined as duration between the date of the first Anti-EpCAM infusion (alternatively in the sensitivity analysis: date of randomization) and the date of clinical disease progression, i.e. the first incidence of progressive disease according to RECIST. If no clinical disease progression was observed, the time span to the date of study termination was taken. In case the date of study termination was not available, the date of the last visit performed was taken instead.

Analysis of Kaplan-Maier (KM–) curves for time to progression is presented in FIGS. 6-8 (time from start of treatment to clinical disease progression).

Overall Anti-EpCAM high dose showed a significant prolongation of the time to progression over time when compared to the Anti-EpCAM low dose treatment (as shown in FIG. 6; Hazard ratio (HR)=0.666). This difference was statistically significant when testing the "survival" curves (p=0.0465; log rank test). Similar, a trend towards a difference in time to progression (calculated as time from first infusion) was observed when comparing patients with low/intermediate versus high EpCAM expression (FIG. 7; HR=0.706; p=0.1157; log rank test). The highest risk reduction time to progression (calculated as time from first infusion) was observed in patients with high EpCAM expression treated with high dose of Anti-EpCAM (HR=0.433; p=0.0057; log rank test—compared to patients with low EpCAM expression treated with low dose of Anti-EpCAM) (as shown in FIG. 8).

Efficacy Conclusions

Based on the study protocol

The best overall response (OTR)

The clinical benefit rate (CBR); and

The time to progression (TTP)

were analyzed comparing the high dose Anti-EpCAM group and the low dose Anti-EpCAM group in the overall population and the low- and high-EpCAM subgroups:

The clinical benefit rates at weeks 12 and 24 (W12 and W24, respectively) could be established comprising all patients showing stable disease at the respective time points.

At W12 the CBR was slightly higher in the high dose Anti-EpCAM group than in the low dose group (16.7% vs. 14.5%), also showing higher rates in both dosage groups for the high EpCAM subgroups (18.9% vs. 8.6% in the low/intermediate EpCAM expressors).

At W24 the CBR was higher in the high dose Anti-EpCAM group (7.9% vs. 4.5% in the low dose Anti-EpCAM group) also indicating higher rates in both dosage groups for the high EpCAM subgroups (7.3% vs. 3.7% in the low/intermediate EpCAM expressors).

The time to progression analysis in the overall sample showed a prolongation for the Anti-EpCAM high dose compared to the Anti-EpCAM low dose (R=0.666), the difference being statistically significant when testing the survival curves (p=0.0465, log rank test). The highest prolongation time to progression (calculated as time from first infusion) was observed in patients with high EpCAM expression treated with high dose of Anti-EpCAM (HR=0.433; p=0.0057; log rank test—compared to patients with low EpCAM expression treated with low dose of Anti-EpCAM).

Overall Conclusions

The data available showed long-term disease stabilization (> week 24) in at least 6 patients according to central radiologic review.

As is clearly visible in FIGS. 6-8, the time to progression evaluation showed a prolongation of "survival time" in favor of the high dose Anti-EpCAM population reaching statistical significance. Specifically, as shown in FIG. 8, patients with high EpCAM expression receiving high doses of Anti-EpCAM significantly prolonged progression-free survival.

The invention claimed is:

1. A method of treating human metastatic breast cancer, said method comprising administering to a human diagnosed with metastatic breast cancer an anti-EpCAM antibody comprising SEQ ID NOs: 3, 4, 5, 6, 7 and 8, respectively, wherein said subject exhibits high EpCAM expression showing a total immunostaining score for EpCAM of greater than 4, wherein said antibody is administered according to a low dose administration schedule comprising administering at least one loading dose in a range of 1 to 3 mg/kg body weight, followed by multiple maintenance doses, each maintenance dose being in a range of 1 to 3 mg/kg body weight, or a high dose administration schedule comprising administering at least one loading dose in a range of 4.5 to 8 mg/kg body weight, followed by multiple maintenance doses, each maintenance dose being in a range of 4.5 to 8 mg/kg body weight.

2. The method of claim 1, wherein the anti-EpCAM antibody comprises SEQ ID Nos: 1 and 2.

3. The method of claim 1, wherein the treatment comprises long-term stabilization of metastatic breast cancer.

4. The method according to claim 1, wherein metastatic breast cancer is classified as Stage IV according to the Tumor Node Metastasis ("TNM") system.

5. The method of claim 1, wherein said anti-EpCAM antibody is administered as at least one loading dose of 2 mg/kg body weight followed by multiple maintenance doses, each maintenance dose being 2 mg/kg body weight.

6. The method of claim 1, wherein said anti-EpCAM antibody is administered as at least one loading dose of 6 mg/kg body weight followed by multiple maintenance doses, each maintenance dose being 6 mg/kg body weight.

7. The method of claim 1, wherein said/each loading dose/s is/are administered every week and each of said maintenance doses is administered every second week.

8. The method of claim 7, wherein one loading dose is administered at the beginning of each of therapy weeks 1, 2 and 3 followed by 11 maintenance doses, one maintenance dose being administered at the beginning of each of therapy weeks 4, 6, 8, 10, 12, 14, 16, 18, 20, 22 and 24.

9. The method of claim 1, wherein the antibody is administered in a solution comprising 0.9% sodium chloride.

10. The method of claim 1, wherein the antibody is administered intravenously.

11. The method of claim 1, wherein said method further comprises administering said anti-EpCAM antibody for a total therapeutic period of 30 weeks, 40 weeks, 50 weeks or 60 weeks.

12. The method of claim 8, wherein said method further comprises administering said anti-EpCAM antibody for a total therapeutic period of 30 weeks, 40 weeks, 50 weeks or 60 weeks.

13. The method of claim 5, wherein said/each loading dose/s is/are administered every week and each of said maintenance doses is administered every second week.

14. The method of claim 6, wherein said/each loading dose/s is/are administered every week and each of said maintenance doses is administered every second week.

15. The method of claim 1, wherein said anti-EpCAM antibody is administered as at least one loading dose in a range of 1.5 to 2.5 mg/kg body weight followed by multiple maintenance doses, each maintenance dose being in a range of 1.5 to 2.5 mg/kg body weight.

16. The method of claim 1, wherein said anti-EpCAM antibody is administered as at least one loading dose in a range of 4.5 to 8 mg/kg body weight followed by multiple maintenance doses, each maintenance dose being in a range of 4.5 to 8 mg/kg body weight.

17. The method of claim 15, wherein said/each loading dose/s is/are administered every week and each of said maintenance doses is administered every second week.

18. The method of claim 16, wherein said/each loading dose/s is/are administered every week and each of said maintenance doses is administered every second week.

* * * * *